United States Patent
Robinette et al.

(10) Patent No.: US 8,965,732 B2
(45) Date of Patent: Feb. 24, 2015

(54) ATHLETIC OR OTHER PERFORMANCE SENSING SYSTEMS

(71) Applicant: Nike, Inc., Beaverton, OR (US)

(72) Inventors: Christopher A. Robinette, Alameda, CA (US); Hector Moll-Carrillo, San Francisco, CA (US); Matt Capozzi, Portland, OR (US); Michael T. Hoffman, Portland, OR (US); Tomislav Lakovic, Portland, OR (US)

(73) Assignee: Nike, Inc., Beaverton, OR (US)

( * ) Notice: Subject to any disclaimer, the term of this patent is extended or adjusted under 35 U.S.C. 154(b) by 0 days.

(21) Appl. No.: 13/974,716

(22) Filed: Aug. 23, 2013

(65) Prior Publication Data

US 2013/0337978 A1    Dec. 19, 2013

Related U.S. Application Data

(62) Division of application No. 12/417,327, filed on Apr. 2, 2009, now Pat. No. 8,517,896.

(60) Provisional application No. 61/041,896, filed on Apr. 2, 2008.

(51) Int. Cl.
| | |
|---|---|
| *G01C 22/00* | (2006.01) |
| *G01C 21/00* | (2006.01) |
| *A63B 24/00* | (2006.01) |
| *A63B 69/00* | (2006.01) |
| *A63B 71/06* | (2006.01) |

(52) U.S. Cl.
CPC ............. *G01C 22/00* (2013.01); *A63B 24/00* (2013.01); *A63B 69/0028* (2013.01); *A63B 2071/0663* (2013.01); *A63B 2220/17* (2013.01); *A63B 2220/34* (2013.01); *A63B 2225/02* (2013.01)
USPC ........................................ 702/160; 377/24.2

(58) Field of Classification Search
USPC ............ 482/1, 3, 4, 7, 8, 9; 235/105; 702/160
See application file for complete search history.

(56) References Cited

U.S. PATENT DOCUMENTS

| | | | |
|---|---|---|---|
| 1,169,999 | A | 2/1916 | Richards |
| 1,170,767 | A | 2/1916 | Lott |
| 1,559,165 | A | 10/1925 | Hammond |
| 1,851,491 | A | 3/1932 | Brown |

(Continued)

FOREIGN PATENT DOCUMENTS

| | | |
|---|---|---|
| WO | 2007064735 A2 | 6/2007 |
| WO | 2009033034 A1 | 3/2009 |

OTHER PUBLICATIONS

Chinese Office Action received in corresponding Application No. 200980115509.8, dated Apr. 28, 2012.

(Continued)

*Primary Examiner* — Loan H Thanh
*Assistant Examiner* — Sundhara Ganesan
(74) *Attorney, Agent, or Firm* — Banner & Witcoff Ltd.

(57) ABSTRACT

A wearable device has a carrier having an aperture. A device has a USB connection and a protrusion wherein the protrusion is received in the aperture to connect the device to a wristband. The device is a USB type device having athletic functionality. The device may further be configured to receive calibration data such that a measured distance may be converted to a known distance based on athletic activity performed by a user.

13 Claims, 29 Drawing Sheets

(56) References Cited

U.S. PATENT DOCUMENTS

| | | |
|---|---|---|
| 2,237,675 A | 4/1941 | Lazrus |
| 2,240,993 A | 5/1941 | Lazrus |
| 2,255,999 A | 9/1941 | Kuehner |
| 2,629,981 A | 3/1953 | Melik-Minassiantz |
| 2,653,442 A | 9/1953 | Kupchick |
| 2,749,634 A | 6/1956 | Billett et al. |
| 3,009,381 A | 11/1961 | Rapata |
| 3,034,189 A | 5/1962 | Twentier |
| 3,208,238 A | 9/1965 | Spitzer |
| 3,421,341 A | 1/1969 | Hodge |
| 3,668,890 A | 6/1972 | Broido |
| 3,677,450 A | 7/1972 | Hodgson |
| 3,769,726 A | 11/1973 | Spence |
| 3,786,391 A | 1/1974 | Mathauser |
| 3,983,690 A | 10/1976 | McClintock |
| 4,048,796 A | 9/1977 | Sasaki |
| 4,055,755 A | 10/1977 | Nakamura et al. |
| 4,059,956 A | 11/1977 | Maeda et al. |
| 4,064,688 A | 12/1977 | Sasaki et al. |
| 4,090,353 A | 5/1978 | Maeda et al. |
| 4,120,036 A | 10/1978 | Maeda et al. |
| 4,139,837 A | 2/1979 | Liljenwall et al. |
| 4,198,772 A | 4/1980 | Furutu |
| 4,207,479 A | 6/1980 | Yamamoto et al. |
| 4,247,929 A | 1/1981 | Sasaki et al. |
| 4,255,802 A | 3/1981 | Ogawa |
| 4,257,115 A | 3/1981 | Hatuse et al. |
| 4,257,117 A | 3/1981 | Besson |
| 4,300,204 A | 11/1981 | Maeda et al. |
| 4,322,833 A | 3/1982 | Husted |
| 4,477,797 A | 10/1984 | Nakagiri |
| 4,578,769 A | 3/1986 | Frederick |
| 4,611,368 A | 9/1986 | Battersby |
| 4,671,671 A | 6/1987 | Suetaka |
| 4,770,008 A | 9/1988 | Yamaura |
| 4,974,429 A | 12/1990 | Ferrara |
| 5,088,070 A | 2/1992 | Shiff |
| 5,410,784 A | 5/1995 | Katz |
| 5,487,053 A | 1/1996 | Beiswenger et al. |
| 5,640,857 A | 6/1997 | Halik |
| 5,689,867 A | 11/1997 | Katz |
| 5,722,260 A | 3/1998 | Mangano |
| 5,758,443 A | 6/1998 | Pedrazzini |
| 5,790,477 A | 8/1998 | Hauke |
| 5,940,349 A | 8/1999 | Stewart |
| 6,077,193 A | 6/2000 | Buhler et al. |
| 6,085,449 A | 7/2000 | Tsui |
| 6,158,884 A | 12/2000 | Lebby et al. |
| 6,215,985 B1 | 4/2001 | Tolvanen |
| 6,243,870 B1 | 6/2001 | Graber |
| 6,324,053 B1 | 11/2001 | Kamijo |
| 6,331,965 B1 | 12/2001 | Sato et al. |
| 6,359,838 B1 | 3/2002 | Taylor |
| 6,446,466 B1 | 9/2002 | Headley |
| 6,477,117 B1 | 11/2002 | Narayanaswami et al. |
| 6,510,988 B1 | 1/2003 | Kraus |
| 6,522,534 B1 | 2/2003 | Wu |
| 6,525,997 B1 | 2/2003 | Narayanaswami et al. |
| 6,527,610 B1 | 3/2003 | Hornsby et al. |
| 6,535,941 B1 | 3/2003 | Kruse |
| 6,556,222 B1 | 4/2003 | Narayanaswami |
| 6,585,622 B1 | 7/2003 | Shum et al. |
| 6,603,708 B2 | 8/2003 | Tamagawa et al. |
| 6,619,835 B2 | 9/2003 | Kita |
| 6,639,791 B2 | 10/2003 | Su |
| 6,701,583 B1 | 3/2004 | McCullough |
| 6,714,486 B2 | 3/2004 | Biggs |
| 6,728,166 B2 | 4/2004 | Grupp |
| 6,733,329 B2 | 5/2004 | Yang |
| 6,736,759 B1 | 5/2004 | Stubbs et al. |
| 6,743,030 B2 | 6/2004 | Lin et al. |
| 6,745,069 B2 | 6/2004 | Nissilä et al. |
| 6,760,003 B1 | 7/2004 | Sase |
| 6,763,410 B2 | 7/2004 | Yu |
| 6,773,192 B1 | 8/2004 | Chao |
| 6,801,476 B2 | 10/2004 | Gilmour |
| 6,804,977 B1 | 10/2004 | Grabelle |
| 6,816,440 B2 | 11/2004 | Born et al. |
| D502,216 S | 2/2005 | Chen |
| 6,895,261 B1 | 5/2005 | Palamides |
| 6,963,468 B2 | 11/2005 | Chang et al. |
| 6,967,903 B2 | 11/2005 | Guanter |
| 6,970,157 B2 | 11/2005 | Siddeeq |
| 6,977,868 B2 | 12/2005 | Brewer et al. |
| 6,980,204 B1 | 12/2005 | Hawkins et al. |
| 6,983,888 B2 | 1/2006 | Weng |
| 6,997,852 B2 | 2/2006 | Watterson et al. |
| 7,006,408 B2 | 2/2006 | Chen |
| 7,029,193 B1 | 4/2006 | Chao |
| 7,030,735 B2 | 4/2006 | Chen |
| 7,031,226 B2 | 4/2006 | Farine |
| 7,031,228 B2 | 4/2006 | Born et al. |
| 7,035,170 B2 | 4/2006 | Narayanaswami et al. |
| 7,042,804 B2 | 5/2006 | Guanter |
| 7,057,551 B1 | 6/2006 | Vogt |
| 7,079,452 B2 | 7/2006 | Harrison |
| 7,081,905 B1 | 7/2006 | Raghunath |
| 7,113,451 B1 | 9/2006 | Matthey |
| 7,177,234 B1 | 2/2007 | Paul |
| 7,221,624 B2 | 5/2007 | Harrison, Jr. |
| 7,234,010 B2 | 6/2007 | Gilmour |
| D545,896 S | 7/2007 | Qiu |
| D547,374 S | 7/2007 | Deng |
| 7,242,639 B2 | 7/2007 | Blondeau et al. |
| 7,254,516 B2 * | 8/2007 | Case et al. .................. 702/182 |
| D553,130 S | 10/2007 | Fiorentino |
| 7,280,844 B2 | 10/2007 | Ikeda et al. |
| 7,293,332 B2 | 11/2007 | Maillard |
| 7,311,526 B2 | 12/2007 | Rohrbach et al. |
| 7,331,793 B2 | 2/2008 | Hernandez et al. |
| 7,351,066 B2 | 4/2008 | DiFonzo et al. |
| 7,603,255 B2 | 10/2009 | Case, Jr. et al. |
| 2003/0148797 A1 | 8/2003 | Huang |
| 2003/0197678 A1 | 10/2003 | Siddeeq |
| 2003/0208382 A1 | 11/2003 | Westfall |
| 2003/0214885 A1 | 11/2003 | Powell et al. |
| 2004/0103000 A1 | 5/2004 | Owurowa et al. |
| 2004/0151071 A1 | 8/2004 | Kocher |
| 2004/0198554 A1 | 10/2004 | Orr et al. |
| 2004/0233786 A1 | 11/2004 | Ting |
| 2004/0264301 A1 | 12/2004 | Howard et al. |
| 2005/0007337 A1 | 1/2005 | Sellen et al. |
| 2005/0075213 A1 | 4/2005 | Arick |
| 2005/0083315 A1 | 4/2005 | Pei |
| 2005/0108059 A1 | 5/2005 | Tay |
| 2005/0209887 A1 | 9/2005 | Pollner |
| 2005/0227811 A1 | 10/2005 | Shum et al. |
| 2005/0228244 A1 | 10/2005 | Banet |
| 2005/0235539 A1 | 10/2005 | Story |
| 2006/0010012 A1 | 1/2006 | Franzblau et al. |
| 2006/0012566 A1 | 1/2006 | Siddeeq |
| 2006/0015368 A1 | 1/2006 | Hockey |
| 2006/0022833 A1 | 2/2006 | Ferguson et al. |
| 2006/0035480 A1 | 2/2006 | Boyd et al. |
| 2006/0063980 A1 | 3/2006 | Hwang et al. |
| 2006/0080137 A1 | 4/2006 | Chambers et al. |
| 2006/0088171 A1 | 4/2006 | Yeh |
| 2006/0092177 A1 | 5/2006 | Blasko |
| 2006/0103642 A1 | 5/2006 | Hawkins et al. |
| 2006/0136173 A1 | 6/2006 | Case et al. |
| 2006/0140055 A1 | 6/2006 | Ehrsam et al. |
| 2006/0145663 A1 | 7/2006 | Shiff et al. |
| 2006/0170649 A1 | 8/2006 | Kosugi et al. |
| 2006/0221772 A1 | 10/2006 | Vuilleumier et al. |
| 2006/0261958 A1 | 11/2006 | Klein |
| 2007/0016452 A1 | 1/2007 | Wilson |
| 2007/0021269 A1 | 1/2007 | Shum |
| 2007/0030442 A1 | 2/2007 | Howell et al. |
| 2007/0033717 A1 | 2/2007 | Anderson |
| 2007/0033838 A1 | 2/2007 | Luce et al. |
| 2007/0058295 A1 | 3/2007 | Lasser |
| 2007/0064542 A1 | 3/2007 | Fukushima |
| 2007/0066088 A1 | 3/2007 | Rambosek et al. |
| 2007/0071643 A1 | 3/2007 | Hall et al. |

(56) References Cited

U.S. PATENT DOCUMENTS

| | | | |
|---|---|---|---|
| 2007/0072442 A1 | 3/2007 | DiFonzo et al. | |
| 2007/0073178 A1 | 3/2007 | Browning et al. | |
| 2007/0080935 A1 | 4/2007 | Hanson et al. | |
| 2007/0100935 A1 | 5/2007 | Miyazaki et al. | |
| 2007/0104032 A1 | 5/2007 | Falkenstein et al. | |
| 2007/0208544 A1* | 9/2007 | Kulach et al. | 702/189 |
| 2007/0221140 A1 | 9/2007 | Warren et al. | |
| 2007/0245465 A1 | 10/2007 | Neal et al. | |
| 2007/0271065 A1* | 11/2007 | Gupta et al. | 702/160 |
| 2007/0287302 A1 | 12/2007 | Lindberg et al. | |
| 2008/0046179 A1 | 2/2008 | Mackintosh et al. | |
| 2008/0214360 A1 | 9/2008 | Stirling et al. | |
| 2008/0254944 A1 | 10/2008 | Muri et al. | |
| 2009/0143689 A1 | 6/2009 | Berry et al. | |
| 2010/0095209 A1 | 4/2010 | Gupta et al. | |
| 2010/0210421 A1 | 8/2010 | Case, Jr. et al. | |

OTHER PUBLICATIONS

The Second Office Action for related Chinese patent application No. 200980115509.8 issued Dec. 17, 2012.
Notice of Reasons for Rejection for Japanese patent application No. 2011-503176 mailed Dec. 6, 2012.
Office Action issued in corresponding Chinese patent application No. 200980115509.8 dated Apr. 28, 2012.
European office action for application No. 09727318.9 mailed Sep. 1, 2011.
International Preliminary Report on Patentability for application No. PCT/US2009/039313 mailed Oct. 14, 2010, 8 pages.
International Search Report and Written Opinion for application No. PCT/US2008/075419 mailed Dec. 23, 2008, 17 pages.
International Search Report and Written Opinion for application No. PCT/US2009/039313 mailed Jul. 3, 2009, 14 pages.
The Third Office Action in Chinese patent application No. 200980115509.8 mailed Aug. 21, 2013.

* cited by examiner

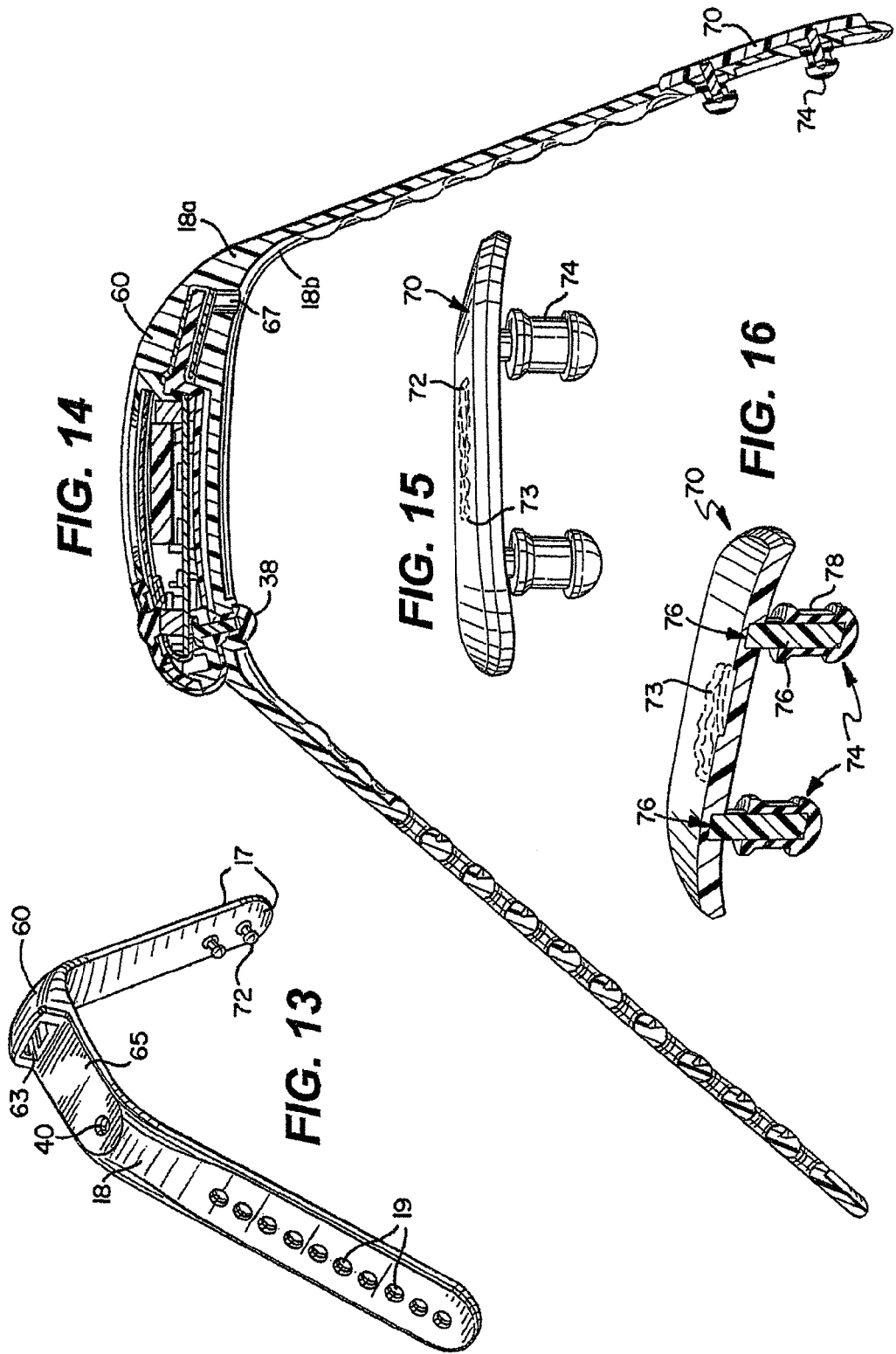

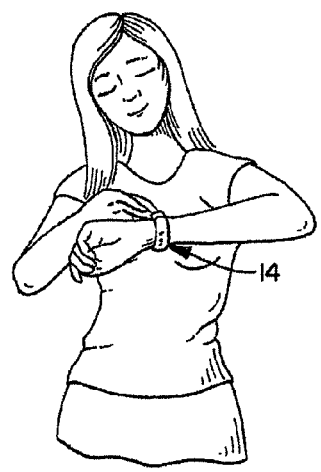
FIG. 17
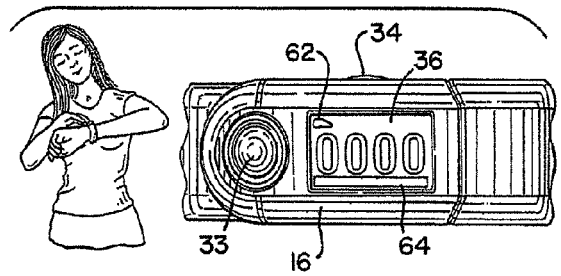
FIG. 18
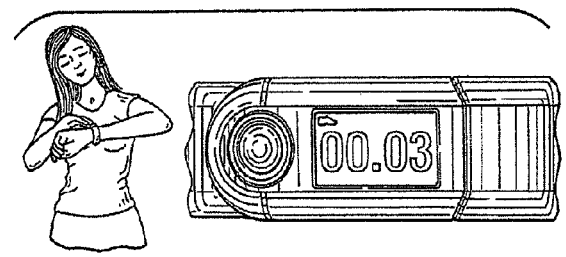
FIG. 19
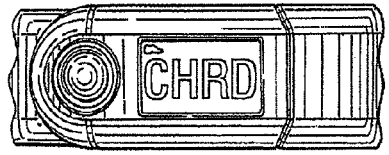
FIG. 20

SETTINGS WINDOW

TIME TAB

| User | Time | Calibration |
|---|---|---|

For each shoe sensor, walk or run a known distance at a steady pace, then adjust if needed.

Recent Runs            --

| | 8.23.09 | 2.10 mi |
|---|---|---|
Recent Walks | 8.25.09 | 0.25 mi
| | 8.26.09 | 0.50 mi |
| | 8.28.09 | 1.52 mi |
| | 9.01.09 | 2.47 mi |
| | 9.03.09 | 2.57 mi |
| | 9.05.09 | 2.47 mi |

Learn about calibration ⓘ  [DONE]

FIG. 82

| User | Time | Calibration |
|---|---|---|

For each shoe sensor, walk or run a known distance at a steady pace, then adjust if needed.

Recent Runs [ 8.23.08    2.10 mi ⇕ ]

Actual Distance [ 2.10 ]⇕ [ miles    ⇕ ]

[ APPLY ]  [ CANCEL ]

Learn about calibration ⓘ  [DONE]

ATHLETIC OR OTHER PERFORMANCE SENSING SYSTEMS

RELATED APPLICATIONS

The present application claims the benefit of and is a divisional of U.S. patent application Ser. No. 12/417,327 filed Apr. 2, 2009, which is a non-provisional application of U.S. Patent Application No. 61/041,896 filed on Apr. 2, 2008. Both applications are incorporated by reference herein in their entirety and made a part hereof.

TECHNICAL FIELD

The invention relates generally to a USB type device, and more particularly, to a wearable USB type device having athletic functionality.

BACKGROUND OF THE INVENTION

Exercise and fitness have become increasingly popular and the benefits from such activities are well known. Various types of technology have been incorporated into fitness and other athletic activities. For example, a wide variety of portable electronic devices are available for use in fitness activity such as MP3 or other audio players, radios, portable televisions, DVD players, or other video playing devices, watches, GPS systems, pedometers, mobile telephones, pagers, beepers, etc. Many fitness enthusiasts or athletes use one or more of these devices when exercising or training to keep them entertained, provide performance data or to keep them in contact with others etc.

Advances in technology have also provided more sophisticated athletic performance monitoring systems. Athletic performance monitoring systems enable easy and convenient monitoring of many physical or physiological characteristics associated with exercise and fitness activity, or other athletic performances including, for example, speed and distance data, altitude data, GPS data, heart rate, pulse rate, blood pressure data, body temperature, etc. This data can be provided to a user through a portable electronic device carried by the user. For example, one athletic performance monitoring system may incorporate an audio player wherein data can be incorporated for display or further communication on the audio player. While athletic performance monitoring systems according to the prior art provide a number of advantageous features, they nevertheless have certain limitations. For example, some users prefer not to use a portable audio player or prefer to obtain and display performance data separately from an audio player. Other athletic performance monitoring systems have limited ability to further upload data to a personal computer or other location for further review and consideration, or such data transfer is cumbersome for the user. The present invention seeks to overcome certain of these limitations and other drawbacks of the prior art, and to provide new features not heretofore available.

A full discussion of the features and advantages of the present invention is deferred to the following detailed description, which proceeds with reference to the accompanying drawings.

SUMMARY OF THE INVENTION

The following presents a general summary of aspects of the invention in order to provide a basic understanding of at least some of its aspects. This summary is not an extensive overview of the invention. It is not intended to identify key or critical elements of the invention or to delineate the scope of the invention. The following summary merely presents some concepts of the invention in a general form as a prelude to the more detailed description provided below.

The present invention provides a USB type device having athletic functionality.

According to one aspect of the invention, a USB device is used as part of an assembly having a carrier wherein the USB device is wearable. In addition, the USB device has a controller that communicates with a sensor to record and monitor athletic performance as an overall athletic performance monitoring system.

According to an aspect of the invention, the USB device is connected to a carrier that in one exemplary embodiment is a wristband. The USB device and wristband have cooperative structure to removably connect the USB device to the wristband. In one exemplary embodiment, the USB device has a protrusion and the wristband has an aperture. The protrusion is inserted into the aperture wherein the USB device is connected to the wristband. It is understood that the protrusion/aperture structures could be reversed on the components.

According to a further aspect of the invention, the wristband has a removable closure. The closure has an indicia-bearing plate having posts that cooperate with openings in the wristband to secure the wristband on a user. The closure is removable wherein different closures bearing different indicia can be utilized with the wristband.

According to another aspect of the invention, the USB device has a housing supporting a controller therein. The housing has a structural configuration wherein the housing is water-resistant as well as impact resistant.

According to another aspect of the invention, the controller utilizes a user interface having certain features to enhance the functionality of the device. The USB device has a display wherein performance data can be displayed to the user. The USB device can be plugged into a computer wherein performance data can be automatically uploaded to a remote site for further display and review.

According to a further aspect of the invention, the controller has software associated therewith and having a calibration module. The calibration module is configured to be operably associated with the device and configured to display a measured distance traversed by the user during an athletic performance. The user can compare the measured distance to a known distance associated with the athletic performance and adjust the measured distance to correspond to the known distance. In a further aspect, based on the adjusted distance, the software saves such adjustment to the device and adjusts how the device records data associated with future athletic performances to enhance the accuracy of the recording of the device.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 13 is a perspective view of the carrier or wristband of the device assembly of FIG. 3 and having the device of FIG. 6 removed;

FIG. 14 is a cross-sectional view of the device assembly of FIG. 3;

FIG. 15 is a perspective view of a removable closure used with the wristband;

FIG. 16 is a schematic cross-sectional view of the removable closure shown in FIG. 15;

FIG. 17 is a partial perspective view of a runner setting the device;

FIG. 18 is a schematic view of the runner setting the device and a plan view of the device indicating that the device is ready to start;

FIG. 19 is a schematic view of the runner starting the device and a plan view of the device indicating time elapsed;

FIG. 20 is a schematic view of the runner and plan view of the device indicating the device is in a data recording mode;

FIGS. 80-85 disclose additional views of a calibration module associated with the software and wearable device assembly of the present invention.

DETAILED DESCRIPTION

Figure 1:
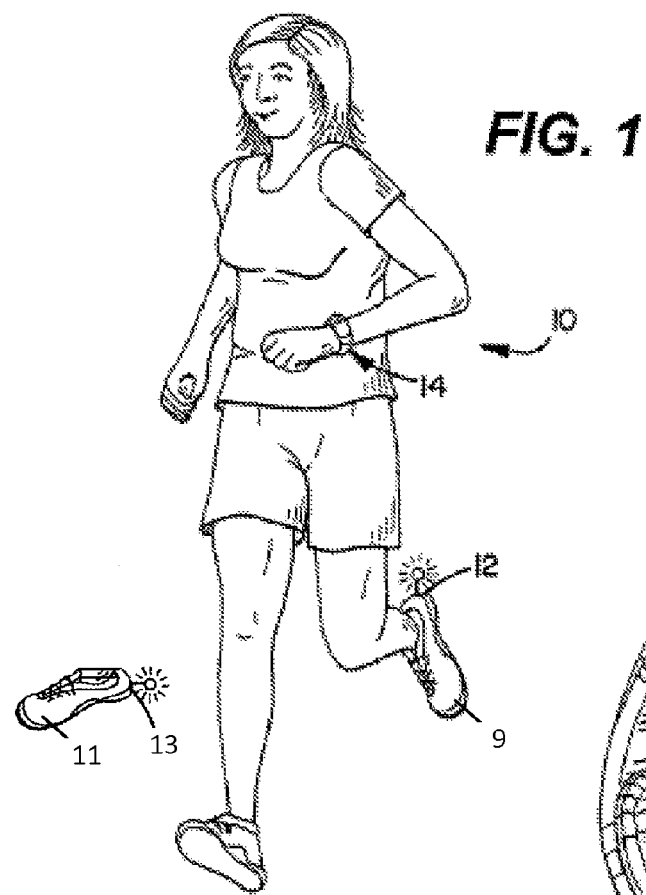
FIG. 1 is a perspective view of a runner wearing a device assembly of the present invention used in an athletic performance monitoring system.
Figure 2:
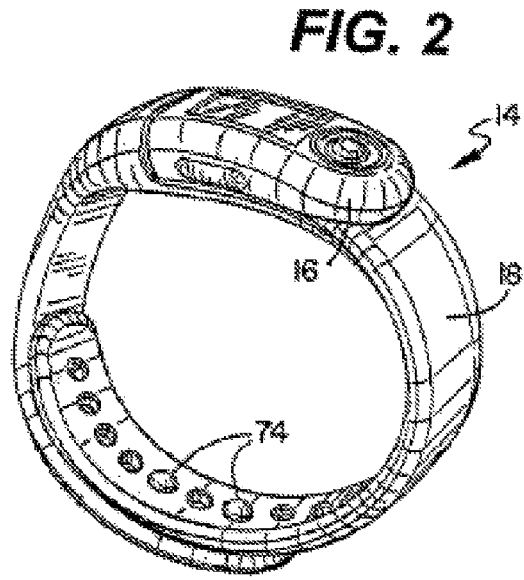
FIG. 2 is a perspective view of the wearable device assembly shown in FIG. 1.
Figure 3:
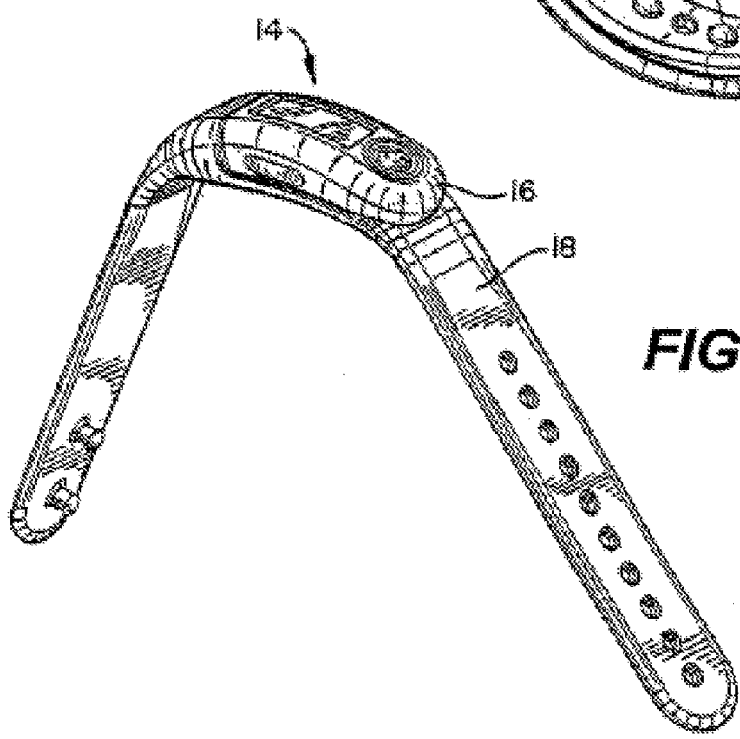
FIG. 3 is a perspective view of the wearable device assembly shown in FIG. 1, with a wristband of the device in an unfastened position.
Figure 4:
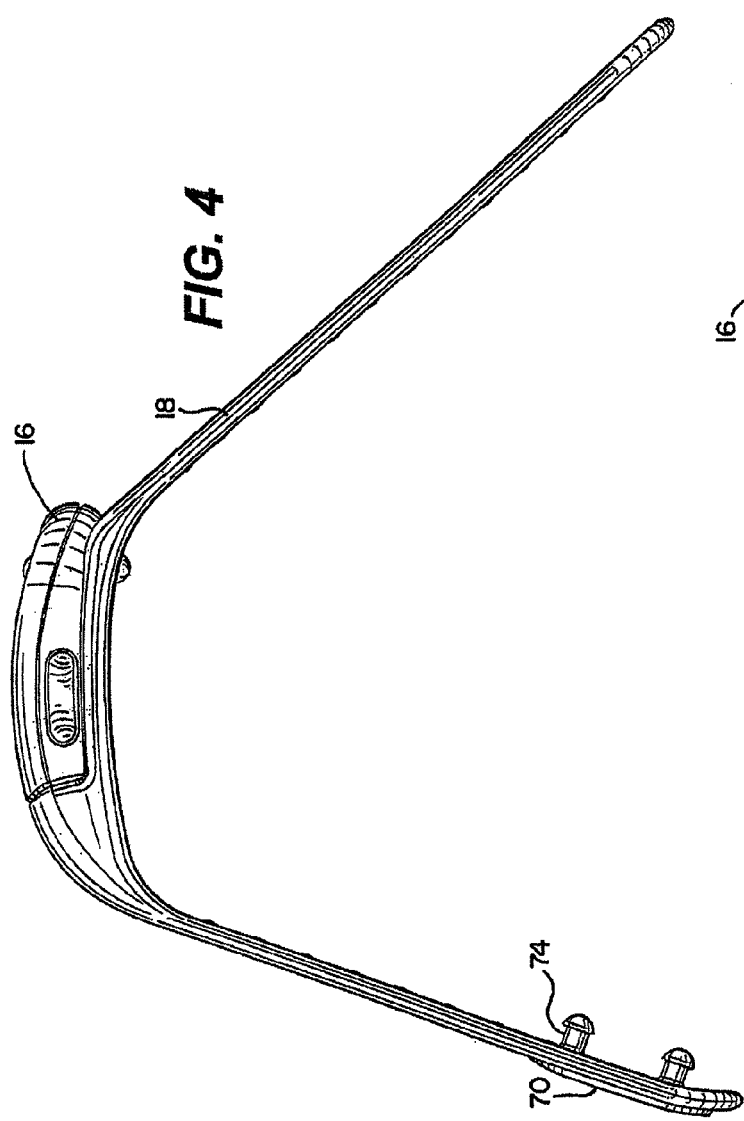
FIG. 4 is a side elevation view of the device assembly shown in FIG. 3.
Figure 5:
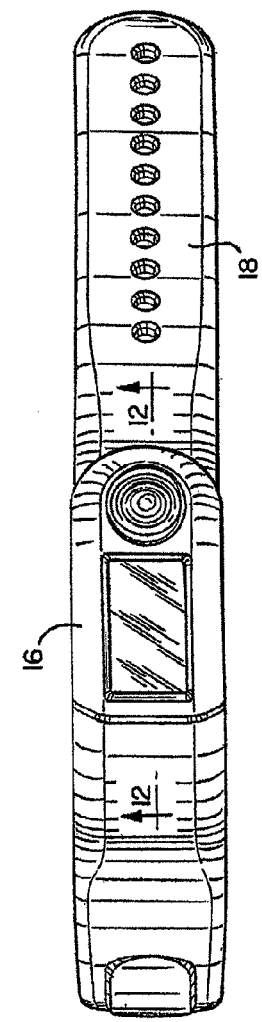
FIG. 5 is a plan view of the device assembly shown in FIG. 3.
Figure 6:
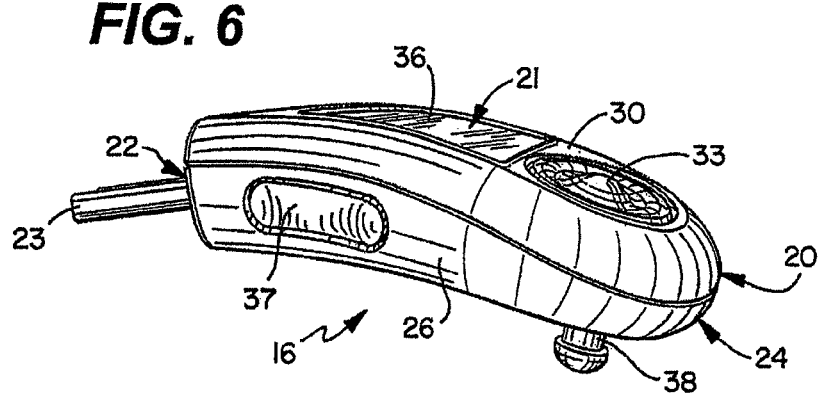
FIG. 6 is a perspective view of a USB-type device of the wearable device assembly.
Figure 7:
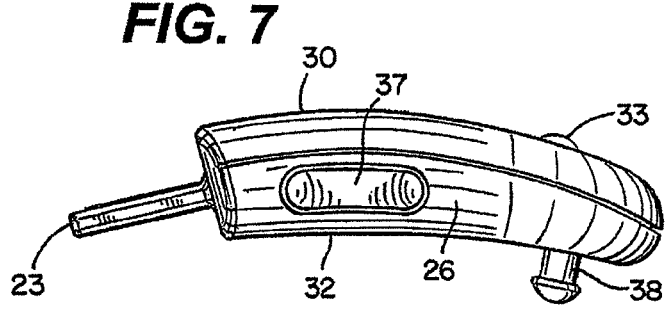
FIG. 7 is a side elevation view of the device shown in FIG. 6.
Figure 8:
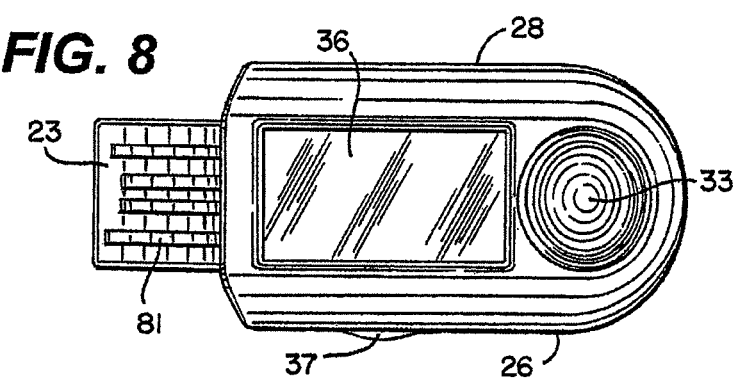
FIG. 8 is a top plan view of the device shown in FIG. 6.
Figure 9:
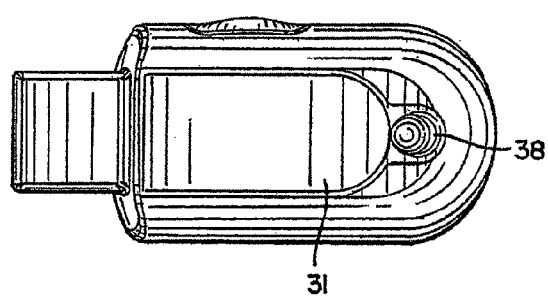
FIG. 9 is a bottom plan view of the device shown in FIG. 6.
Figure 10:
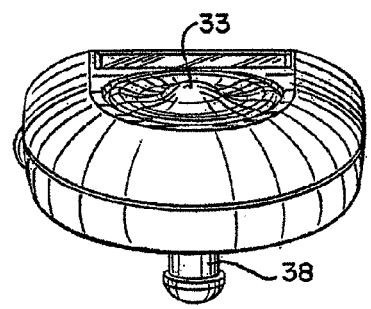
FIG. 10 is an end view of the device shown in FIG. 6.
Figure 11:
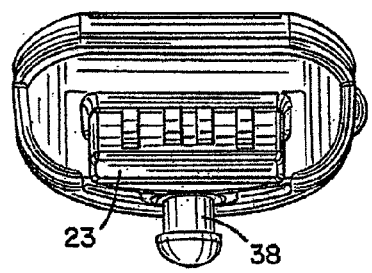
FIG. 11 is an opposite end view of the device shown in FIG. 6.

In the following description of various example embodiments of the invention, reference is made to the accompanying drawings, which form a part hereof, and in which are shown by way of illustration various example devices, systems, and environments in which aspects of the invention may be practiced. It is to be understood that other specific arrangements of parts, example devices, systems, and environments may be utilized and structural and functional modifications may be made without departing from the scope of the present invention. Also, while the terms "top," "bottom," "front," "back," "side," and the like may be used in this specification to describe various example features and elements of the invention, these terms are used herein as a matter of convenience, e.g., based on the example orientations shown in the figures. Nothing in this specification should be construed as requiring a specific three dimensional orientation of structures in order to fall within the scope of this invention.

General Description of Aspects of the Invention

The present invention provides a USB device having athletic functionality. In one exemplary embodiment, the USB device is as part of an assembly having a carrier wherein the USB device is wearable. In addition, the USB device has a controller that communicates with a sensor to record and monitor athletic performance as an overall athletic performance monitoring system.

The USB device is connected to a carrier that in one exemplary embodiment is a wristband. The USB device and wristband have cooperative structure to removably connect the USB device to the wristband. In one exemplary embodiment, the USB device has a protrusion and the wristband has an opening. The protrusion is inserted into the opening wherein the USB device is connected to the wristband. The wristband has a removable closure. The closure has an indicia-bearing plate having posts that cooperate with openings in the wristband to secure the wristband on a user. The closure is removable wherein different closures bearing different indicia can be utilized with the wristband.

The USB device has a housing supporting the controller therein. The housing has a structural configuration wherein the housing is water-resistant as well as impact resistant.

The controller utilizes a user interface having certain features to enhance the functionality of the device. The USB device has a display wherein performance data can be displayed to the user. The USB device can be plugged into a computer wherein performance data can be automatically uploaded to a remote site for further display and review.

In addition, the carrier can take other forms wherein the USB device can be worn by a user in a various different locations.

Specific Examples of the Invention

While aspects of the invention generally have been described above, the following detailed description, in conjunction with the Figures, provides even more detailed examples of athletic performance monitoring systems and methods in accordance with examples of this invention. Those skilled in the art should understand, of course, that the following description constitutes descriptions of examples of the invention and should not be construed as limiting the invention in any way.

FIG. 1 generally discloses an athletic performance monitoring system 10 that in one exemplary embodiment of the invention includes a wearable device having athletic functionality. As shown in FIG. 1, the athletic performance monitoring system 10 generally includes a module or sensor 12 and a wearable device assembly 14. As discussed in greater detail below, the sensor 12 and wearable device assembly 14 wirelessly communicate with one another to record and monitor athletic performance.

The sensor 12 may have various electronic components including a power supply, magnetic sensor element, microprocessor, memory, transmission system and other suitable electronic devices. The sensor 12 in one exemplary embodiment is mounted on the shoe of a user as shown in FIG. 1. The sensor 12 is used in conjunction with the other components of the system to record speed and distance among other parameters of athletic performance. The sensor 12 can be a sensor as disclosed in U.S. Publication Nos. 2007/0006489; 2007/0011919 and 2007/0021269. These U.S. Publications are attached in Appendix A hereto and made a part hereof.

The wearable device assembly 14 generally includes a wearable device 16 that in one exemplary embodiment is a USB (Universal Serial Bus) type device 16, and a carrier 18 that in one exemplary embodiment takes the form of a wristband 18. The device 16 has many features similar to a USB flash drive, but has additional functionality as discussed in greater detail below. In addition, the device 16 is removably connected to the wristband 18.

As depicted in FIGS. 6-12, the wearable device 16 generally includes a housing 20 and a controller 21 that is contained by the housing 20. General components and functional capabilities of the controller 21 will be described in greater detail below. The housing 20 has a first end 22, a second end 24, a first side 26, a second side 28, a front side 30, and a back side 32.

As further shown in FIGS. 6-12, the first end 22 includes a connector 23 that is generally a standard USB connector having leads or contacts embedded therein. The connector 23 is integrally molded with the housing 20 as described in greater below. The connector 23 is adapted to connect to a USB hub of a computer. The front side 30 has a pushbutton 33 that will cooperate with a first input 32 of the controller 21 for controlling the wearable device 16 as described in greater detail below. The first side 26 includes a side opening for accommodating a second input 34 of the controller 21 for controlling the wearable device 16. The front side 30 also accommodates a display 36 of the controller 21. It is understood that the front side 30 of the housing 20 could have an opening wherein a screen of the display is positioned therein.

It is also understood that the housing 20 could be formed such that it has a solid, thin layer wherein the display 36 of the controller 21 is viewable through the thin layer on the front side 30.

Figure 12:
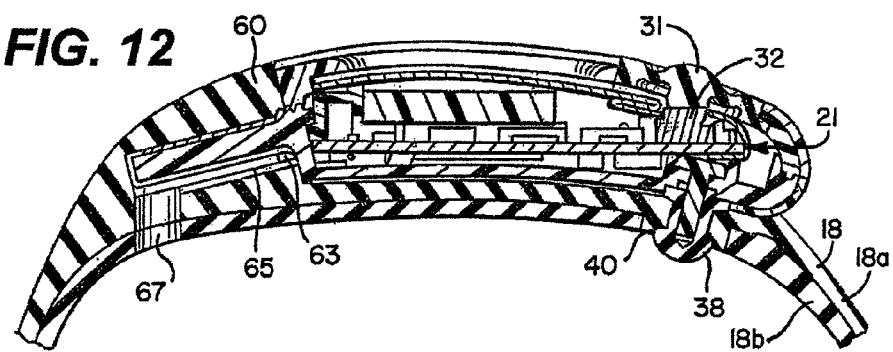
FIG. 12 is a partial cross-sectional view of the device taken along line 12-12 of FIG. 5.
Figure 21:
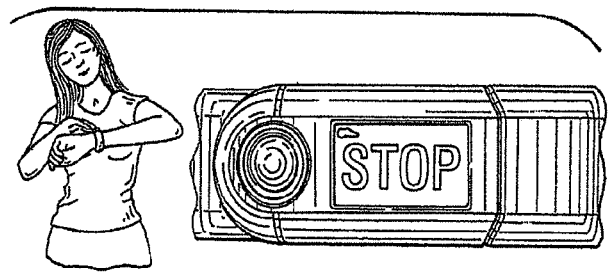
FIG. 21 is a schematic view of the runner stopping the device and a plan view of the device indicating that the device has been stopped.
Figure 22:
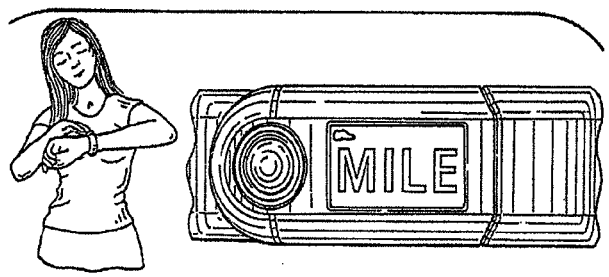
FIG. 22 is a schematic view of the runner reviewing performance data and a plan view of the device preparing to indicate miles run.
Figure 23:
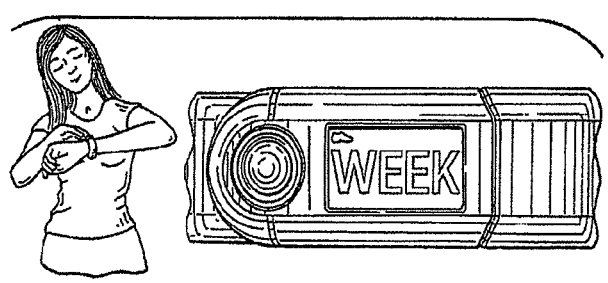
FIG. 23 is a schematic view of the runner reviewing performance data and a plan view of the device preparing to indicate miles run in a week.
Figure 24:
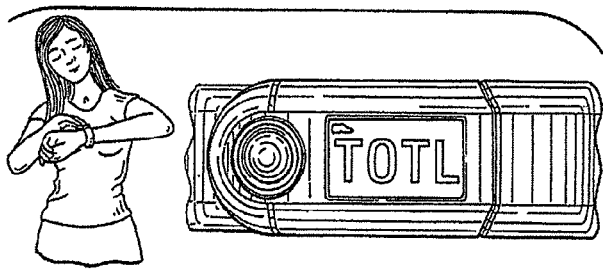
FIG. 24 is a schematic view of the runner reviewing performance data and a plan view of the device preparing to indicate total miles run.
Figure 25:
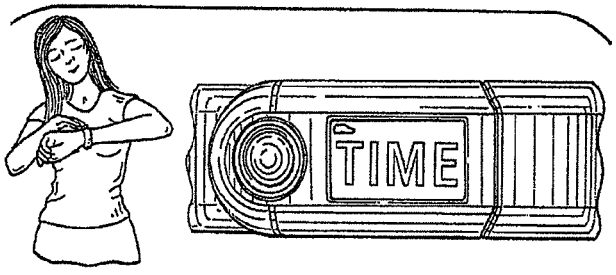
FIG. 25 is a schematic view of the runner reviewing performance data and a plan view of the device preparing to indicate time.

As depicted in FIGS. 6-12, the back side 31 of the housing 20, near the second end 24, has a protrusion 38. The protrusion 38 has a generally circular cross-section. The protrusion 38 has an enlarged rounded head and an insert that fits within the interior of the housing 20 (FIG. 12). As explained in greater detail below, the protrusion 38 is adapted to be inserted into a receiver or aperture 40 in the carrier 18.

As further shown in FIGS. 6-12, the components of the controller 21 are contained within and supported by the housing 20. The controller 21 includes various electrical components allowing the controller 21 and device 16 to act as an interface device wherein the device 16 can communicate with the sensor 12, record and store data relating to athletic performance, other time information, as well as upload performance data to a remote location or site as described in greater detail below. The controller 21 further includes the first input 32 and the second input 34. The controller 21 further includes the display 36 that is positioned on the front side 30 of the housing 20. It is further understood that the controller 21 is operably connected to the connector 23 of the housing.

As shown in FIGS. 2-4 and 12-14, the carrier 18 is generally in the form of a wristband 18 having a central portion between a first end and a second end. The wristband 18 may include a first member 18a and second member 18b generally molded or connected together. The wristband 18 is flexible to fit around a user's wrist. The wristband 18 has receiving structures for connection to the device 16. The carrier 18 includes a protective sleeve 60 proximate the central portion for receiving the connector 23 of the housing 20. The protective sleeve 60 has a generally contoured surface. As shown in FIG. 13, the sleeve 60 may have internal structure for assisting in securing the connector 23. Also at the central portion, the carrier 18 has an aperture 40 dimensioned to receive the protrusion 38 of the wearable device 16.

As further shown in FIGS. 4 and 13-16, the wristband 18 has a removable closure 70 used to fasten the wristband 18 to a wrist of a user. To this end, the removable closure 70 cooperates with a plurality of holes in the wristband 18. The removable closure 70 has a plate member 72 and a plurality of posts 74 extending generally in a perpendicular direction from the plate member 72. In the exemplary embodiment depicted in FIG. 15, the plate member 72 has two posts 74. Each post 74 has an insert 76 that is pressed on or snap-fitted onto the post 74. Each insert 76 is spot welded to the plate member 72. Other connection methods are possible. A gap is maintained between an inside surface of the plate member 72 and a bottom surface of the post 74. In addition, each post 74 has an annular channel 78 around a periphery of the post 74.

To wear the wristband, first the removable closure 70 is connected to one end of the wristband strap 18 wherein a pair of holes is provided to receive the posts 74. The wristband 18 fills the gap. The wristband 18 is positioned around the user's wrist and the posts 74 are inserted into the holes provided on the other end of the wristband 18 as can be appreciated from FIG. 2. The portion of the wristband 18 proximate the holes fits within the annular channels 78 of the posts 74. With the use of a pair of posts 74, the removable closure 70 allows for a secure connection and greater flexibility in connection providing for a greater adjustment to accommodate for a range of wrist sizes.

Additionally, the plate member 72 can have indicia 73 thereon. The plate member 72, when attached to the wristband 18 faces away from the wristband 18 wherein the indicia 73 can be viewed by others. Because the removable closure 70 is easily removable, the closure 70 can be used as a memento, different closures can be provided and used with the wristband 18. Thus, removable closures 70 having different indicia can be provided and used as a keepsake, memento, or a reward for accomplishing a goal, participating in a race, or otherwise achieving a certain level of fitness. Indicia can take various forms including wording, graphics, color schemes, textures, or other designs etc.

As discussed, the wearable device 16 is removably connected to the carrier 18. The connector 23 is inserted into the sleeve 60 of the carrier 18, and the protrusion 38 is placed into the aperture 40 of the carrier 18. The enlarged head of the protrusion abuts against the wristband 18 to retain the device 16 onto the wristband 18. This provides for a wearable device 16 that can be disconnected from the carrier 18 when desired and plugged into a computer as discussed in greater detail below. It is understood that detent structures can be provided between the connector 23 and sleeve 60 of the various different embodiments disclosed herein.

It is understood that the device 16 has general functions such as keeping the time of day just like a convention watch device. It is further understood, however, that the device 16 can be used as part of the athletic performance monitoring system 10. For example, a user wearing shoes having the sensor 12 mounted therein can use the device 16 to wirelessly communicate with the sensor 12 and monitor performance such as for running.

As can be appreciated from FIGS. 17-27, when the user wants to start a run, the user must first allow the sensor 12 to communicate with the wearable device 16. To do this, the user pushes and holds the first input 32 via the pushbutton 33 on the front side 30 of the housing 20. While the user holds the first input 32, the display 36 exhibits scrolling zeros as the wearable device 16 searches for the sensor 12. Once the sensor 12 is located, as shown in FIG. 18, the display 36 indicates that the wearable device 16 is ready to start by displaying a shoe symbol 62 in the upper left corner and a blinking underline 64. The user then pushes the first input 32 again to initiate the recording of the run. The wearable device 16 then records various information during the run such as elapsed time as shown in FIGS. 19 and 20. A bottom line on the display 36 animates back and forth to indicate that the device 16 is in the record mode. During the run, the user can toggle through the distance ran, current pace, elapsed time, and calories spent by pushing the second input 34. To stop recording, the user pushes the first input 32. After the device 16 is stopped, the user can review the last distance run (FIG. 22), average pace, calories burnt, average calories burnt per minute, miles ran per week (FIG. 23), total miles (FIG. 24), and the time of day of the run (FIG. 25) by pressing the second input 34, which toggles through these values.

Figure 26:
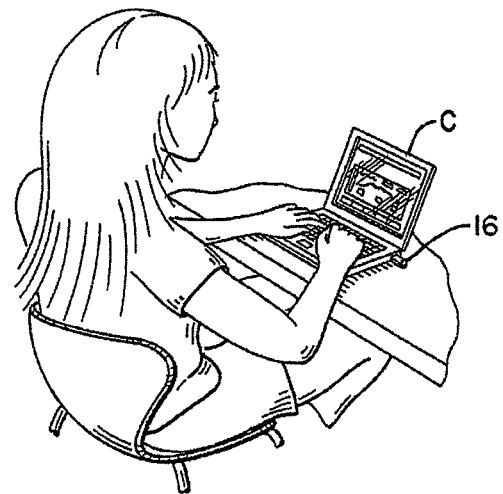
FIG. 26 is a perspective view of the runner at a computer and having the device plugged into the computer.
Figure 27:
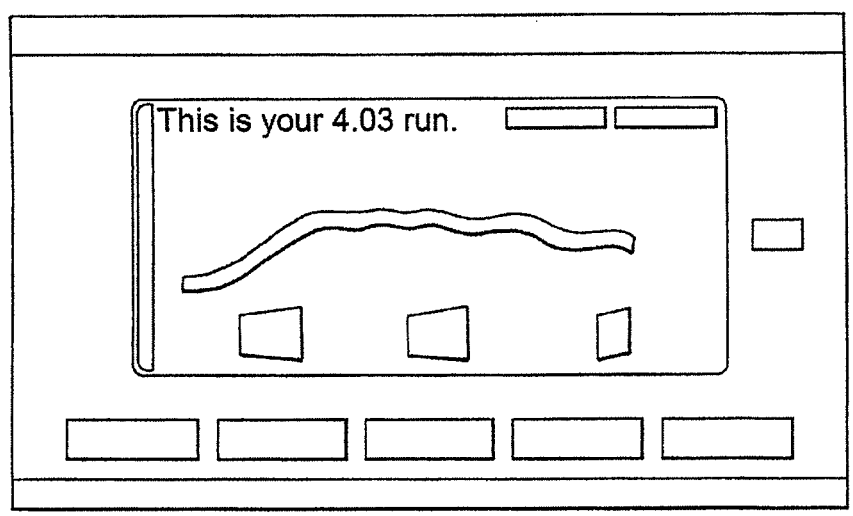
FIG. 27 is a front view of a computer screen displaying performance data recorded by the device.
Figure 28:
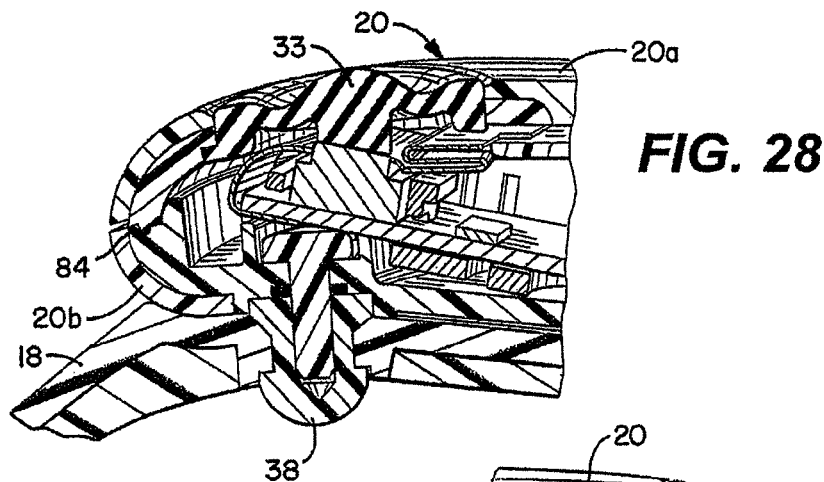
FIG. 28 is a partial cross-sectional view showing an end of the device and carrier.
Figure 29:
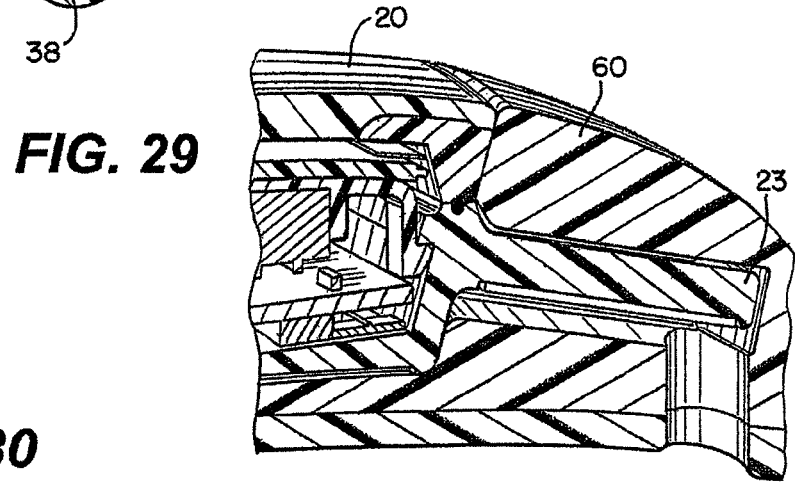
FIG. 29 is a partial cross-sectional view showing a connector end of the device.
Figure 30:
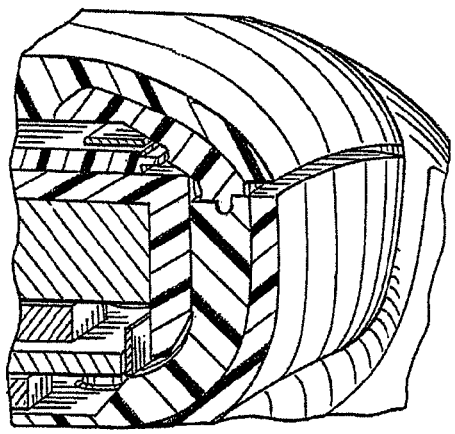
FIG. 30 is another partial cross-sectional view of the device.

The device 16 has additional capability for uploading of the recorded data to other remote locations such as locally on a personal computer or a remote website for further display, review and monitoring. To this end, it is understood that the controller 21 of the device has an appropriate user interface wherein a user can download appropriate software via a computer from a remote location. The device 16 is removed from the carrier 18 wherein the protrusion 38 is removed from the aperture 40 and the connector 23 is removed from the sleeve 60. As shown in FIGS. 26 and 27, the connector 23 is then plugged into the standard USB hub/port on a computer C. Once the appropriate software is installed, the application will commence with device 16 still being plugged into the computer. The software application may prompt the user through a device set-up procedure (time, calibration etc.). At this point, if desired, the user can upload the performance data from the run to a remote website location such as one dedicated to monitoring athletic performance. The user can log onto the particular website via a standard web-browser and upload the performance data from the device 16 to the website. As shown in FIG. 27, the user can then review data relating to the run. The website may display the data in graphical form. Other features can also be provided to assist the user in utilizing the data recorded by the device. Additional registration features can be provided with the website wherein additional features can be provided to the user for use with the device 16.

The user interface associated with the controller 21 of the device 16 can provide additional functionality to the user. The software can include a self launching feature, which automatically launches the software once the wearable device 16 is connected to a computer containing the software. Once the program is launched, the software will also automatically download the data from the device 16 to the computer and transfer the data to a web server and to the website discussed above. The software can also detect the device class connected to the port and configure the correct application for that specific device. For example, there may be wearable devices 16 having different configurations, or technical capabilities, and thus may be classified differently. The software can change the feature set of the fitness activity recording of the wearable device 16 connected to the port of the computer. After the wearable device 16 is disconnected from the computer, the software automatically exits. The user interface may also be configured to allow a user to selectively activate and de-activate features according to the preferences of the user. The user may also be able to modify software associated with the device.

The software has an extremely simple calibration method and user interface. For example, it is very simple to calibrate distance measurements onto the device. A calibration module associated with the software as well being configured to be operably associated with the device assembly 14 and sensor 12 is described in greater detail below. The software can also track motivational information among several classes of fitness activity recording devices. For example, the user can set weekly goals and the software can track the user's progress with these goals. The user can also use multiple devices, such as an audio player having a suitable interface device, other types of sport watches etc., along with the device of the present invention, and the software will accumulate the weekly and overall total distance recorded by all of the devices. Thus, the data is kept synchronized over multiple devices.

The website can additionally have a guest log in, which allows the user to upload data automatically from the device without requiring the user to register. This feature allows the user to use the website without giving personal information. Later, if the user decides to register the device, a unique PIN number associated with each wearable device is matched up with registration information automatically.

As discussed, the wearable device assembly 14 utilizes its housing 20 to support the controller 21 and associated components. In one exemplary embodiment, the housing 20 has unique structures to enhance its functionality. Because the device 16 is used in fitness activities, there is some chance that the device 16 can be subject to water or moisture such as perspiration. The housing 20 is designed to be water-resistant to protect components of the controller 21.

As shown in FIGS. 28-36, the housing 20 has a first member 20a and a second member 20b. The first member 20a is joined with the second member 20b to form the housing 20.

The members 20a, 20b are generally formed from plastic in an injection molding process. It is understood that the housing 20 can be constructed from other suitable materials.

As discussed, the front side 30 of the housing 20 has a first push button 33 that is flexible and cooperates with the first input 34 of the controller 21. In an exemplary embodiment, the first push button 33 is co-molded with the first member 20a. The co-molding process allows for the combination of a hard plastic portion with a soft elastic polymer portion. The hard polymer portion provides the controller 21 with adequate protection from shock or other forces, and the soft elastic polymer portion of the push button 33 allows the user to depress the first push button 33 to actuate the first input 32. With the co-molding process, the first push button 33 is integral with the housing 20. Together the hard polymer portion and the soft elastic polymer portion provide for an adequate sealed structure of the housing 20 around the first push button 33 of the housing 20.

As depicted in FIGS. 32-36, the second member 20b of the housing 20 is formed in an injection molding process having the connector 23 and a U-shaped groove 80. The connector 20 has a plurality of leads or contacts 81 associated therewith making up the USB connection. The connector 23 is integrally molded with the remaining portions of the second member 20b to eliminate the need for a separate connection and seal around the connector 23. The leads 81 can have break-off portions to assist in the molding process. As further shown in FIGS. 27-36, the U-shaped groove 80 is molded into the second member 20b and extends around the full periphery of the second member 20b. The second member 20b also includes locating ribs for assisting in providing an accurate fit between the first member 20a and the second member 20b.

To join the first member 20a and the second member 20b, the necessary components of the controller 21 are suitably mounted in and connected to the second member 20b. The U-shaped groove 80 is filled with an epoxy 84 (shown schematically in FIG. 28). A flexible epoxy suitable for bonding injection molded parts is used. The first member 20a is then placed onto the second member 20b using the locating ribs and the epoxy is allowed to set. Once the epoxy sets, a flexible and water resistant seal is formed between the first member 20a and the second member 20b.

Figure 31:
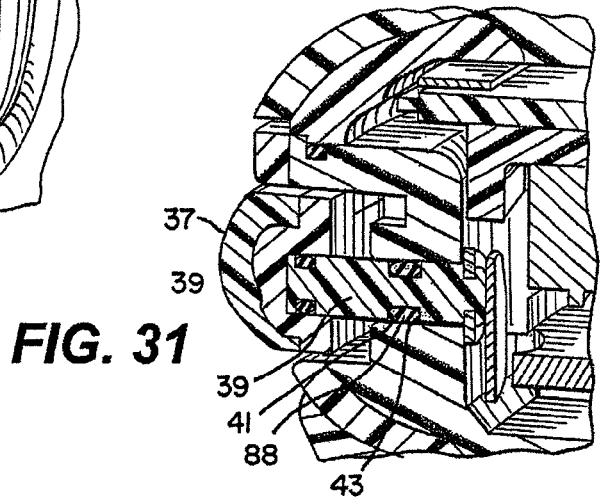
FIG. 31 is a partial cross-sectional view of the device showing an input device.
Figure 32:
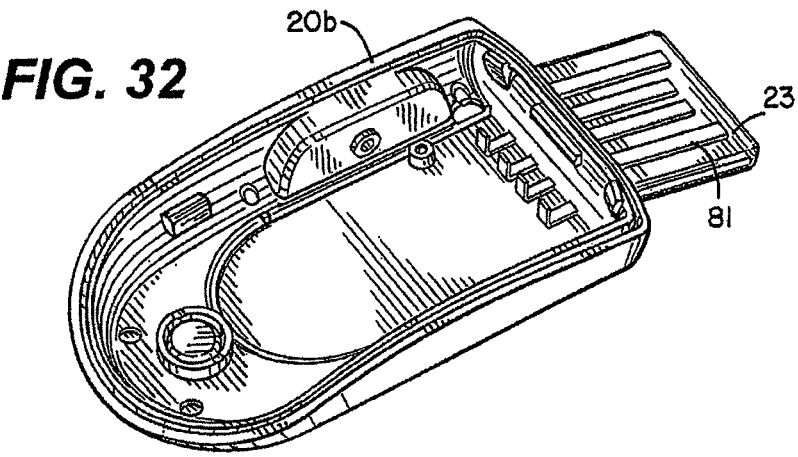
FIG. 32 is a perspective view of a bottom member of a housing of the device shown in FIG. 6.
Figure 33:
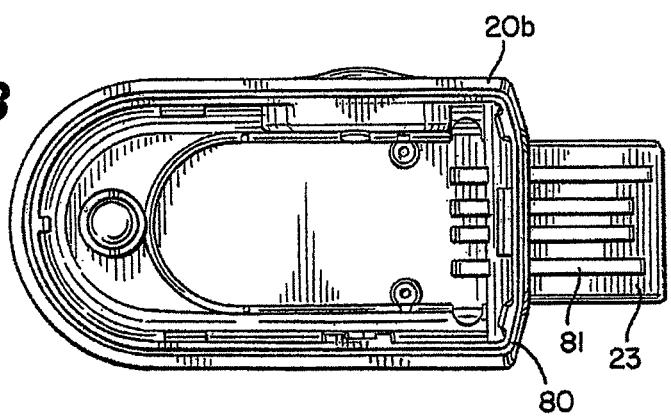
FIG. 33 is a plan view of the bottom member of the housing shown in FIG. 32.
Figure 34:
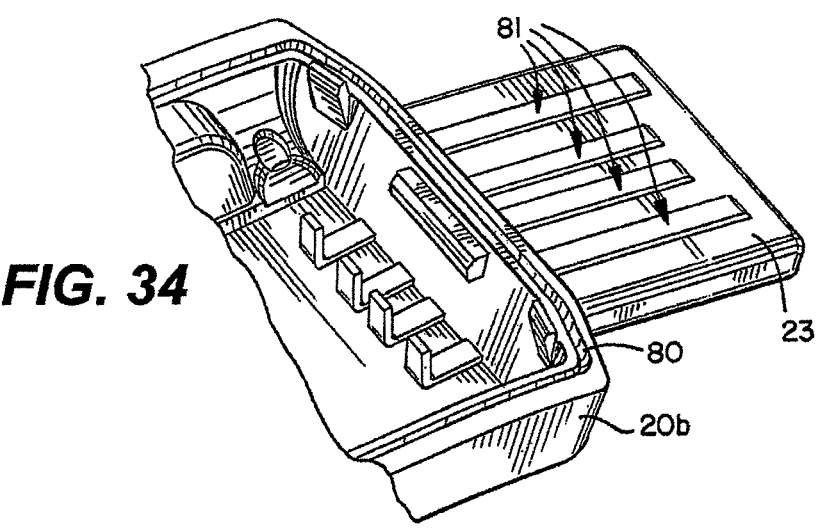
FIG. 34 is a partial perspective view of the bottom member of the housing shown in FIG. 32.
Figure 35:
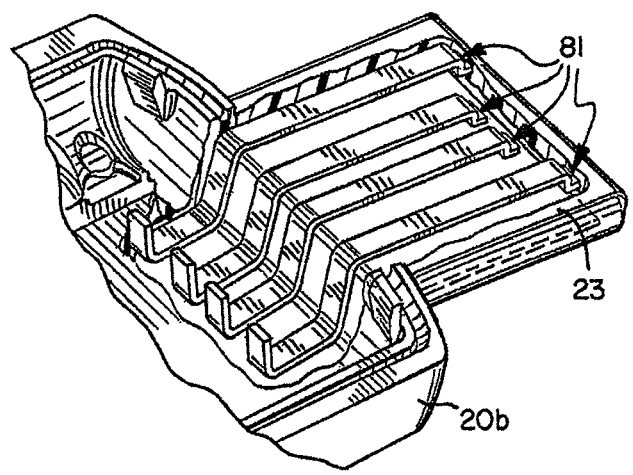
FIG. 35 is partial perspective view of the bottom member of the housing with a portion shown in phantom lines.
Figure 36:
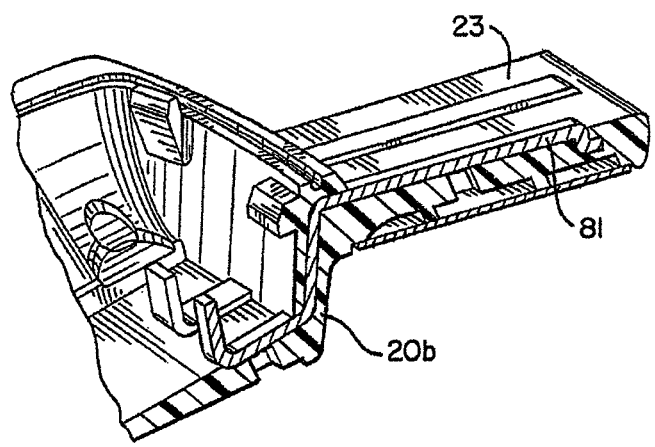
FIG. 36 is a partial cross-sectional view of the bottom member of the housing shown in FIG. 32.
Figure 37:
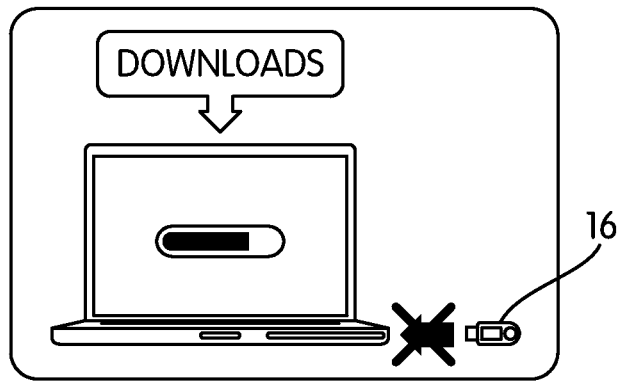
FIGS. 37-50 are views of screen shots from software illustrating operational characteristics of the wearable device assembly of the present invention.
Figure 38:
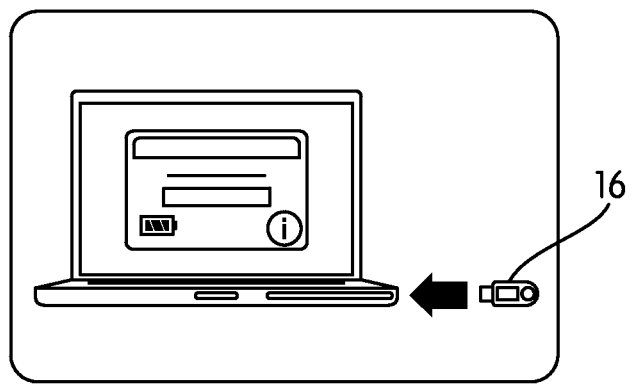
Figure 39:
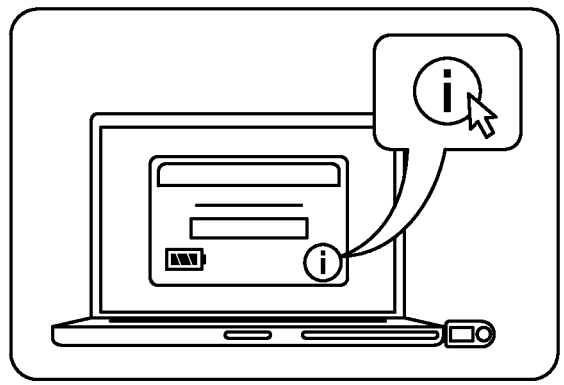
Figure 40:
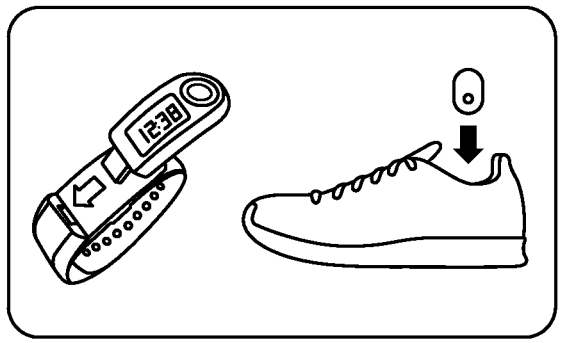
Figure 41:
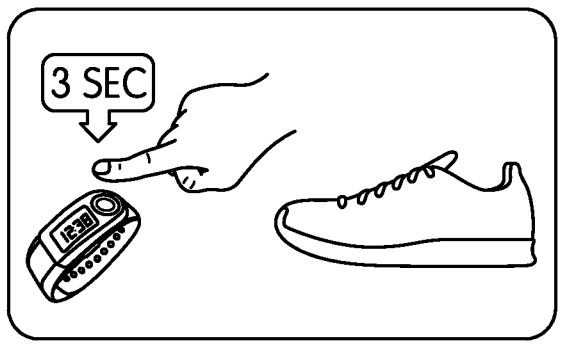
Figure 42:
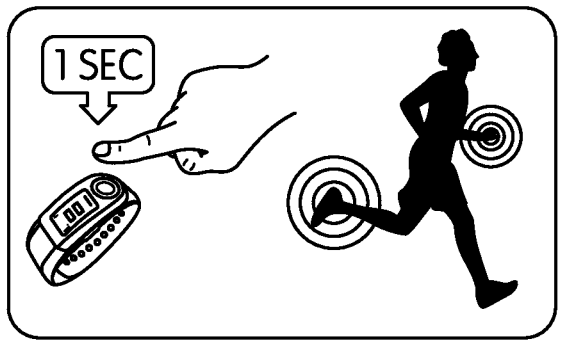
Figure 43:
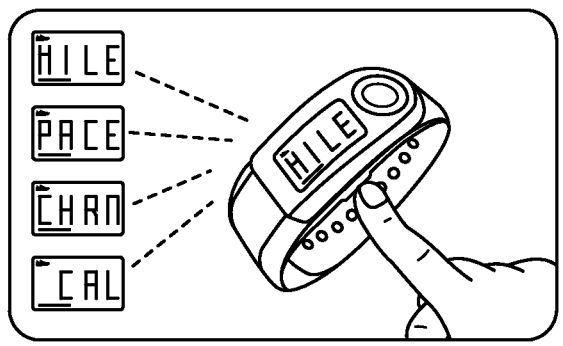
Figure 44:
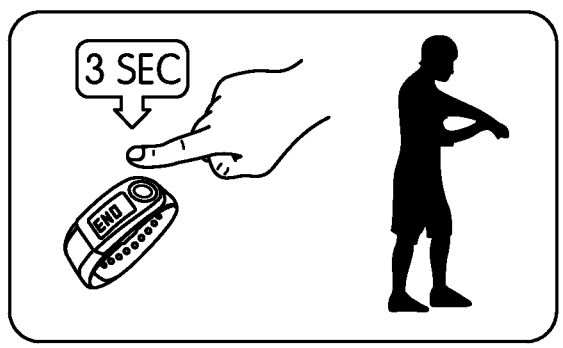
Figure 45:
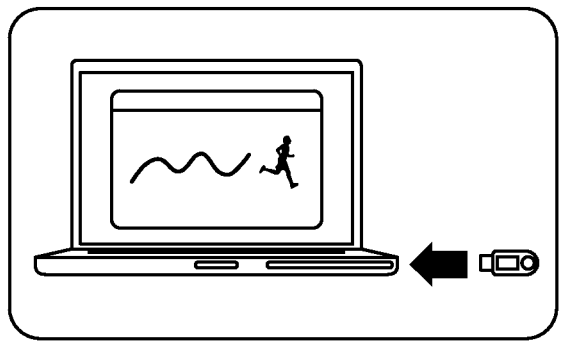
Figure 46:
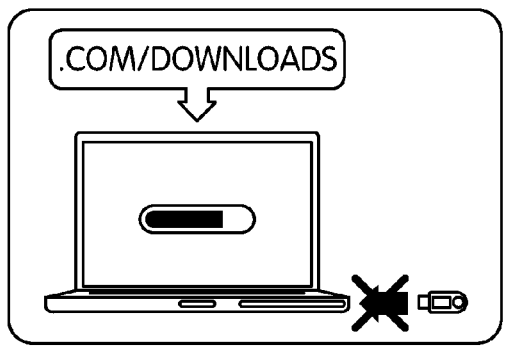
Figure 47:
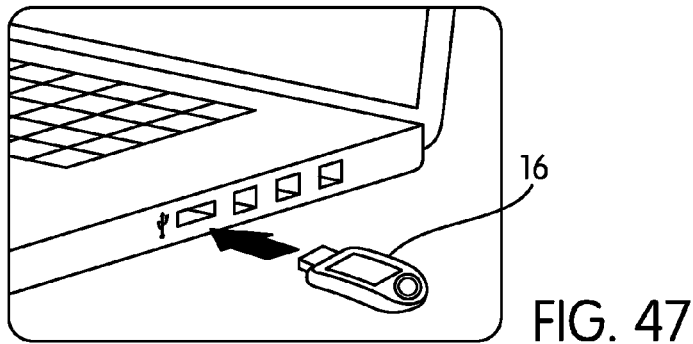
Figure 48:
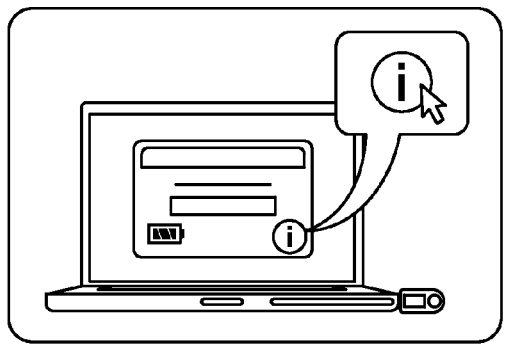
Figure 49:
Figure 50:
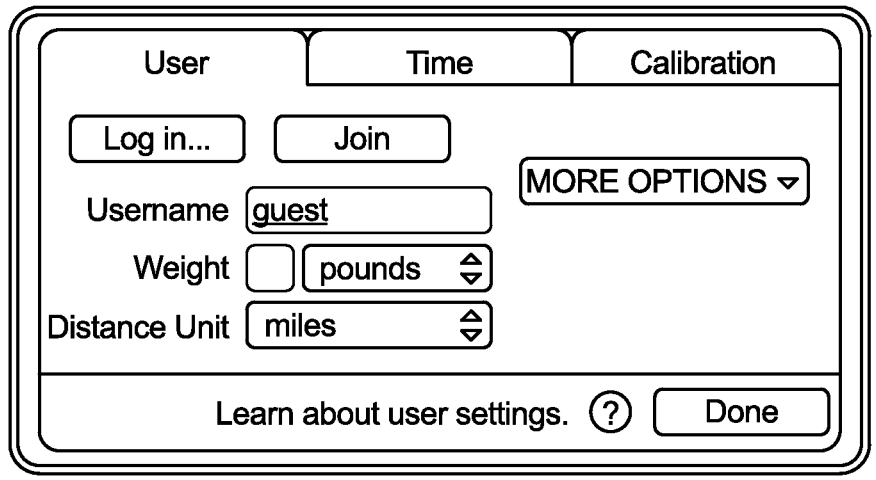

As further shown in FIG. 31, the second input 32 has a second push button 37 associated therewith. The second push button 37 has an actuator post 39 extending therefrom and through the side opening of the housing 20. It is understood that the first member 20a and second member 20b of the housing 20 are molded to define the side opening. The side opening narrows down to a post opening 41 adjacent an interior of the housing 20 for communication with further components of the second input 34. The actuator post 39 has an annular groove 43 around a periphery of the post 39. Additionally, a sealing member such as an o-ring 88 surrounds the actuator post 39 in the annular groove 43. The o-ring 88 is sized to seal against the interior surface defined by the post opening 41. The o-ring 88 provides an adequate seal such that debris, water or other moisture cannot enter the housing 20 through the side opening in the housing 20.

This overall arrangement provides for a robust wearable device. The wearable device housing structure can absorb the shocks and impacts of running such that the controller can operate smoothly. Additionally, the wearable device housing structure prevents debris, water or other moisture from ingress into the interior of the housing where it could contaminate the controller 21 and adversely affect operability. In one exemplary embodiment, the wearable device 16 is water-resistant to approximately five atmospheres of pressure.

FIGS. 37-85 disclose general operational features of the wearable device assembly 14. Included in these features is a calibration module associated with the software and the wearable device assembly 14 and sensor 12.

The figures disclose procedures for the user in the initial setup of the wearable device assembly 14 as well as getting the user started in recording athletic performance data such as run or walk data. This covers the procedures undertaken by the user in getting started with the assembly 14. Procedures for using the Settings Window, the User Tab and Time Tab are also described.

Figure 51:
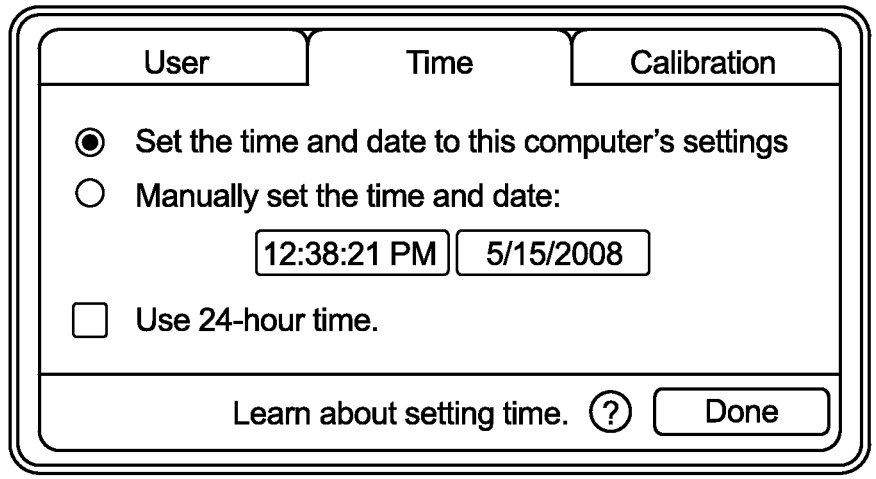
FIGS. 51-53 are views of a calibration module associated with the software and wearable device assembly of the present invention.
Figure 52:
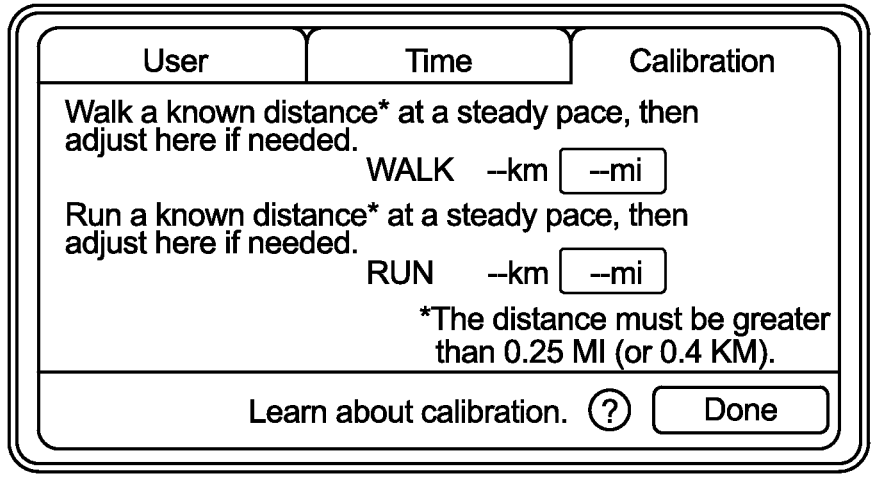
Figure 53:
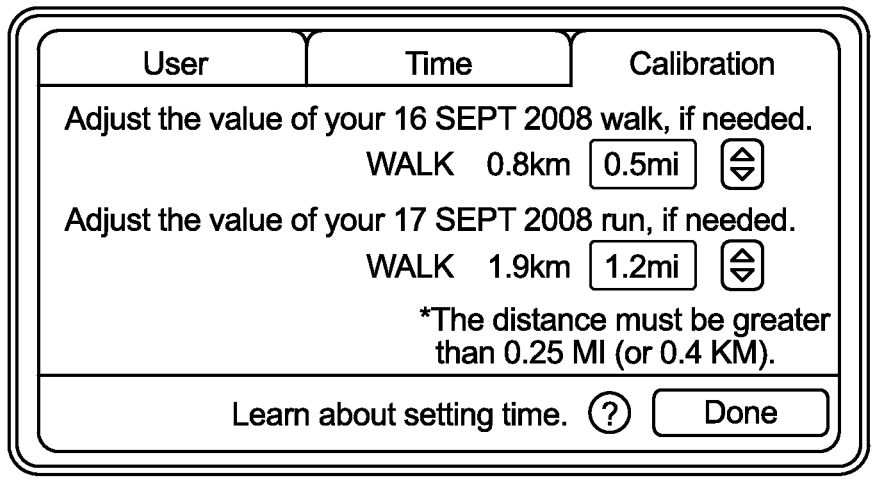

FIGS. 51-53 disclose additional calibration procedures for the assembly 14. While the wearable device assembly 14 is generally accurate for most users without calibration, utilizing the available calibration procedures can improve the accuracy of the assembly 14 for a user's particular running or walking style. The calibration procedure is performed for running or walking separately. As discussed above, the system utilizes associated software such as when uploading athletic performance data to the remote site. The wearable device assembly 14 and software may then have a calibration module associated therewith for a user to implement the calibration procedures. The calibration module is operably associated with the assembly 14 and can reside at various locations including on a desktop utility associated with the user's computer C or at some other remote location such as the remote site as described above.

The user first enables the assembly 14 for recording data as described above and establishes a calibration run or walk by running or walking a known distance at a steady, natural pace. When referring to a run by the user herein, it is understood that this could be either a run or a walk by the user. It is important the distance be measured accurately and, therefore, a running track may be useful for such calibrations as distances are typically marked and are accurate. In one exemplary embodiment, the run or walk is between 0.25 and 1.25 miles. It is understood that the assembly 14 records data from the sensor based on factory set parameters associated with the sensor 12. The assembly 14 records the athletic performance of the user in the form of a run or walk and records a measured distance of the distance traversed by the user. The measured distance corresponds to a measured value and may be recorded in different units such as miles or kilometers. The device 16 is then removed from the assembly 14 and the USB plug is inserted into the USB port on the user's computer C. It is understood that the computer has all of the necessary software downloads etc. for operation as described above. Utilizing the user interface on the computer, the user clicks on the "i" button in the main window. A Settings Window appears and the user clicks on the calibration tab as shown in FIG. 52. A useable run or walk will be displayed in the window including distance and date as shown in FIG. 53. It is understood that a run or walk will not be displayed if there is no usable run or walk, such as if the run or walk was for an incorrect distance or if the user mixed running with walking. In this case, the user interface will provide the message, "no walks or runs were useful" wherein the user must repeat the run or walk until successful.

As shown in FIG. 53, the run or walk can easily be calibrated. For example, if the user knows the run or walk was exactly 1 mile, which represents the known distance, but the Calibration tab setting shows that the user ran or walked just over or just under a mile, which represents the measured distance/value recorded by the assembly 14 in communication with the sensor 12, the user can make adjustments to the measured distance/measured value. As shown in FIG. 53, the user can manually adjust the measured value using the "up"

and "down" buttons so that 1 mile is shown. Thus, the calibration module allows the user to adjust the measured distance to correspond to the known distance. If the distance shown is 1 mile, the user does not need to change the display. The user clicks the "Done" button wherein the changes are saved, the Settings Window is closed and the user is taken back to the main Utility Window. This calibration adjustment is thus saved to the assembly 14 wherein when the assembly 14 is recording data with the associated sensor 12 in subsequent athletic performances, the assembly 14 will record data based on the calibration adjustment recorded and saved by the user. Accordingly, the assembly 14 will have enhanced data recording capabilities based on the user calibration performed. As discussed, the sensor 12 and/or assembly 14 will initially record data at certain set parameters and may be referred to as factory set parameters. Using the calibration module, the user can adjust the distance measured in a calibration run thus defining a modified parameter. This modified parameter is saved to the assembly 14 wherein when the assembly 14 records subsequent athleticperformances, the assembly 14 records data from the sensor 12 based on the modified parameter. It is understood that the assembly 14 and sensor 12 has a calibration value for a run and a separate calibration value for a walk and thus the user must calibrate runs and walks separately. In an exemplary embodiment, the assembly 14 communicates with the sensor 12 to record run/walk data wherein it is understood that there is a linear relationship between foot contact time of the user and pace, wherein foot contact time may be considered a Y-axis value and pace may be considered an X-axis value. A run or walk can be represented by a line utilizing the line algorithm, $y=mx+b$, wherein m equals the slope and b equals the Y-intercept. Thus, based on the line algorithm, data is recorded according to a line having a certain slope. Once the user adjusts or modifies the measured distance to correspond to the known distance, the slope is modified according to the user adjustment. This new slope is saved wherein for subsequent performance data recordings, the assembly 14 will communicate with the sensor 12 to record data at the modified parameter or slope. Such calibration adjustment provides for enhanced data recording capabilities.

The device 16 is capable of storing calibration information for multiple sensors 12 and 13, such as if the user runs or walks in several different pairs of shoes 9 and 11, respectively (FIG. 1). In one exemplary embodiment, the device 16 can accommodate information for up to 8 sensors. Each time the user obtains a new sensor, the calibration procedure described above should be performed. If the user desires to calibrate the device 16 a second time, the user must reset the run or walk in the Calibration tab settings. The user clicks the Reset button to return the device 16 back to the original factory calibration settings. This improves the accuracy of subsequent calibrations. It is further noted that even after calibrating, the accuracy of the distance measurements may vary depending on gait, running surface, incline, or temperature. Also, calibrating a target "race pace" will provide the user better accuracy when running a race.

The assembly 14 also has further calibration capabilities to enhance overall operation. As discussed, users can access and track performance data relating to previous runs or walks. Such data is stored at remote locations such as a website dedicated to such data. In one exemplary embodiment, the overall user interface allows a user to connect a recorded run with a mapped profile. The mapped profile shows the total distance of the run and represents a known distance. When the user makes this connection, the distance of the run can be compared to the measured distance of the run. If these values are different, the user can be prompted to use the mapped distance to calibrate the device 16. Additional windows or buttons can be provided to effect such a change.

In another alternative calibration procedure, the overall user interface allows a user the option to "name a run." When multiple runs (e.g., three runs in one exemplary embodiment) are linked to the same run name, the user interface can use the average of the multiple runs and compare this value to the last distance run. If these values are different, the user interface can prompt the user to use the multi-run average to calibrate the device 16. Thus the multi-run average of prior runs or walks can be used as the known distance for calibration. Additional windows or buttons can be provided to effect such a change.

Figure 81:
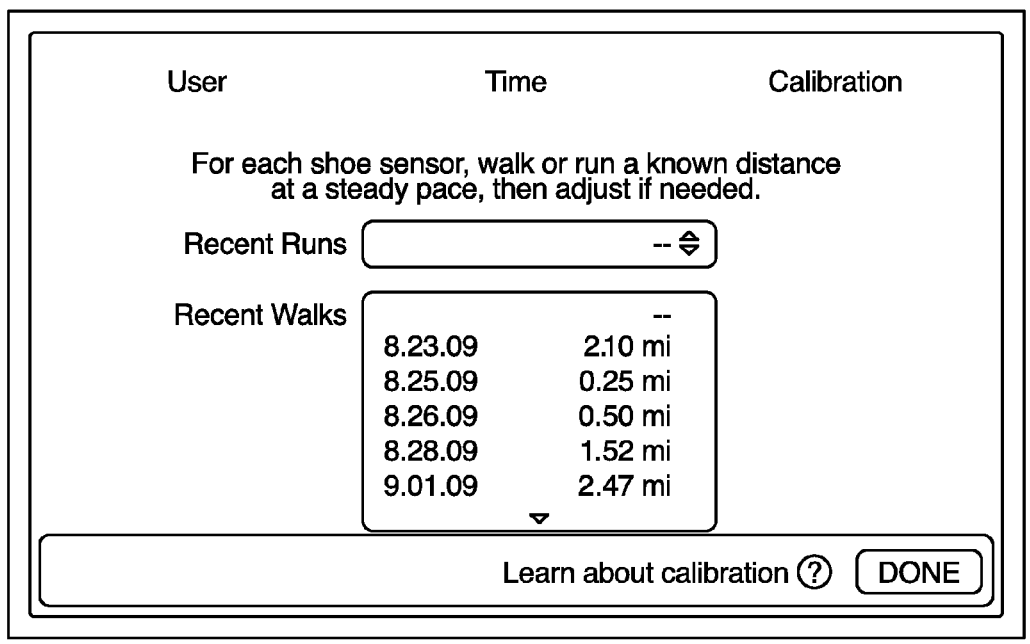
Figure 84:
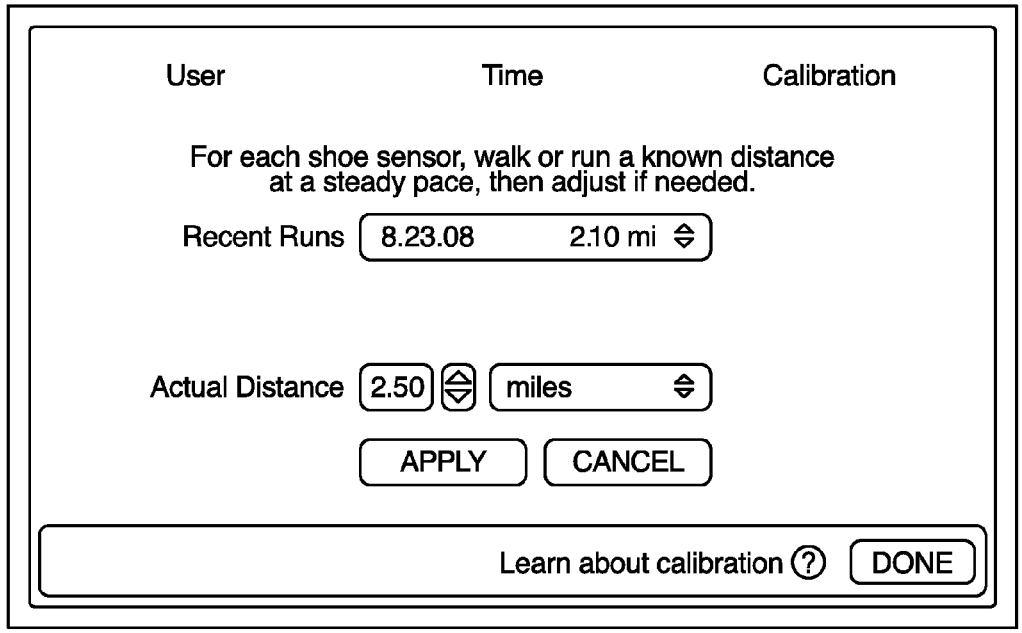
Figure 85:
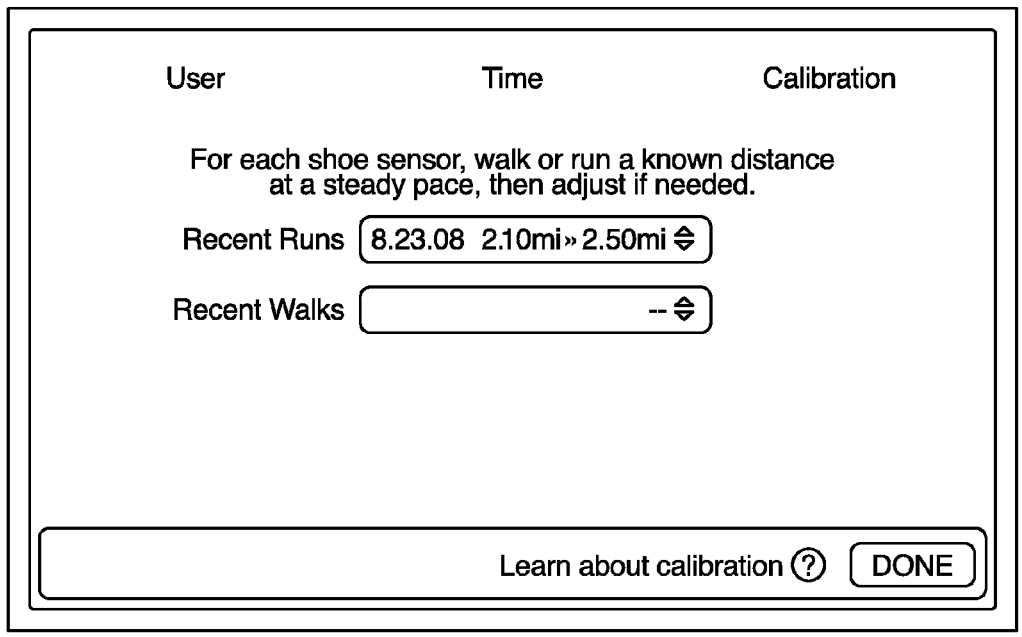

FIGS. 80-85 disclose additional screen shots from the user interface associated with the calibration module of the present invention wherein a run and/or walk recorded with the assembly 14 and sensor 12 can be calibrated. As previously discussed, the assembly 14 has software operably associated therewith that includes the calibration module. As shown in FIG. 81, through the computer C, the user can click on the Calibration tab of the calibration module, wherein a Recent Runs drop down menu is displayed and a Recent Walks drop down menu is displayed. The drop down menus are populated with recent calibration-eligible runs and walks that were uploaded from the assembly 14 as described above. As shown in FIG. 82, it is understood that the drop down menus can expand as needed with up/down arrows wherein the user can scroll through the menus to select a run or walk to calibrate. In an exemplary embodiment, the date of the run or walk is listed with the measured distance adjacent to the date. As can be appreciated from FIG. 83, once a user selects a run or walk field, the other field becomes inactive automatically. Thus, as shown in FIG. 83, once the user selects the 8.23.08 run for example, the selection is highlighted and the Recent Walks field is inactive. Also, an Actual Distance field is displayed along with up/down arrows and the standards of measurement. Thus, the user can change between miles and kilometers if desired. The up/down arrows allow the user to change the Actual Distance value in increments of hundredths. Also, once the 8.23.08 run is selected, the associated measured distance, 2.10 miles, is placed in the Actual Distance field. As shown in FIG. 84, the user can click on the up/down arrows to change the measured distance to correspond to the known distance traversed by the user. As shown in FIG. 84, the user knows the known distance of the 8.23.08 run was 2.5 miles. Thus, the user clicks on the up arrow until the Actual Distance field is adjusted to 2.5 miles. Once the Actual Distance field is adjusted, the Save and Cancel buttons become active and change to a perceptively different color such as the color red. Pressing Cancel returns the user to the screen shown in FIG. 80. Pressing the Apply button enters the information into the memory associated with the calibration module thereby saving the calibration. As shown in FIG. 85, in response to pressing the Apply button, the Recent Runs field displays the 8.23.08 run with the original measured distance (2.10 miles) with the new calibrated distance (2.50 miles) next to the original measured distance. This also provides an indication to the user that this particular run was calibrated.

Consistent with the discussion above, this calibration adjustment shown in FIGS. 80-85 is saved to the assembly 14 wherein when the assembly 14 is recording data with the associated sensor 12 in subsequent athletic performances, the assembly 14 will record data based on the calibration adjustment recorded and saved by the user. Accordingly, the assembly 14 will have enhanced data recording capabilities based on the user calibration performed. As discussed, the sensor 12 and/or assembly 14 will initially record data at a certain set parameter and may be referred to as a factory set parameter. Using the calibration module, the user can adjust the distance measured in a calibration run thus defining a modified parameter. This modified parameter is saved to the assembly 14 wherein when the assembly 14 records subsequent performances, the assembly 14 records data based on the modified parameter. It is understood that the assembly 14 and sensor has a calibration value for a run and a separate calibration value for a walk. In an exemplary embodiment, the assembly 14 communicates with the sensor 12 to record run/walk data wherein it is understood that there is a linear relationship between foot contact time of user and pace, wherein foot contact time may be considered a Y-axis value and pace may be considered an X-axis value. A run or walk can be represented by a line utilizing the line algorithm, $y=mx+b$, wherein m equals the slope and b equals the Y-intercept. Thus, based on the line algorithm, data is recorded according to a line having a certain slope. Once the user adjusts or modifies the measured distance to correspond to the known distance, the slope is modified according to the user modification. This new slope is saved wherein for subsequent performance data recordings, the assembly 14 will communicate with the sensor 12 to record data at the modified parameter or slope. It is understood that the same procedure described above can be done for a walk as well. Such calibration adjustment provides for enhanced data recording capabilities.

In one exemplary embodiment, if the user calibrates a run/walk a second time that utilizes a common sensor, the earlier calibration will be overwritten by the subsequent calibration. The calibration module can also be configured such that subsequent calibrations using a run/walk with the same sensor can be combined with earlier calibrations. In such instances, the data can be combined wherein subsequent calibrations further enhance the calibrations.

In one or more configurations, the line algorithm or formula correlating foot contact time and pace may be modified as new information and athletic performance data becomes available. For example, as discussed herein, an initial line algorithm may be modified based on a run or other athletic activity covering a known distance. If an athlete subsequently performs additional athletic activity traversing the same or another distance, that contact vs. pace distance for that additional athletic activity may be used to modify the line algorithm. The building of the line algorithm may provide better accuracy (e.g., in the event data for a first athletic activity is an outlier). In one example, the athletic performance data of the additional athletic activity may be averaged into the line algorithm.

Additionally or alternatively, the line algorithm may be used to interpolate or extrapolate distance conversions. That is, the line algorithm may be initially generated based on a first athletic activity of a known distance (e.g., 1 mile). If subsequently an athlete performs a second athletic activity of a second measured distance, the contact information or pace data associated with the second athletic activity may be adjusted to match the line algorithm so that a calibrated distance may be determined (e.g., via extrapolation or interpolation).

With the calibration procedures described above, a user can use any run or walk for calibration, and not just a particular run completed in calibration mode. As the procedure is finalized using the personal computer of the user with user friendly prompts, it is much easier for the user to understand and have confidence in the accuracy of the assembly 14.

Figure 54:
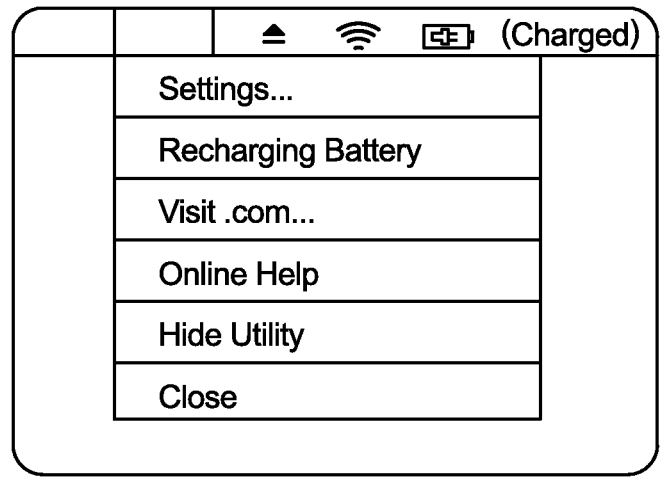
FIGS. 54-55 show additional views of screen shots illustrating operational characteristics of the wearable device assembly of the present invention.
Figure 55:
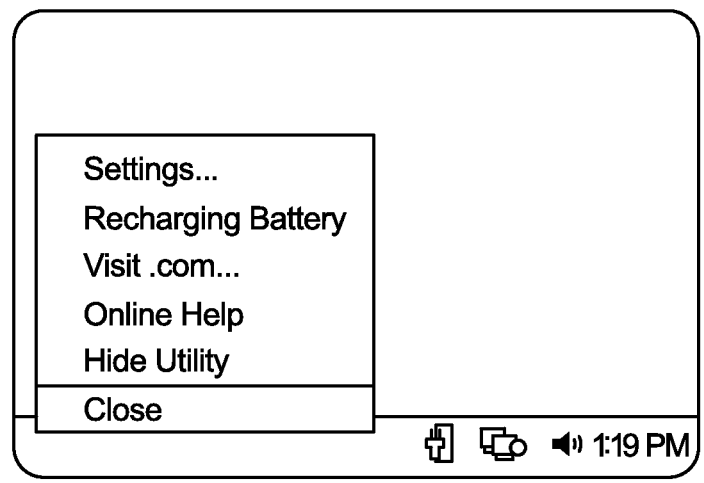
Figure 56:
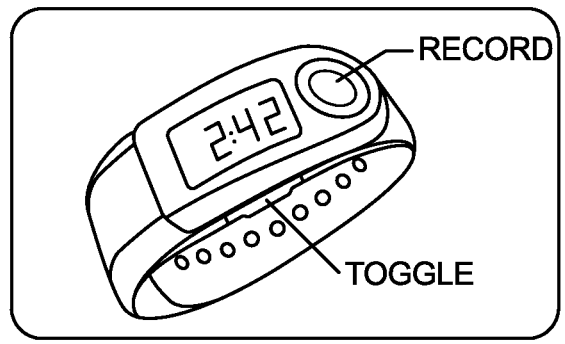
FIGS. 56-79 are views illustrating additional operational characteristics of the wearable device assembly of the present invention.
Figure 57:
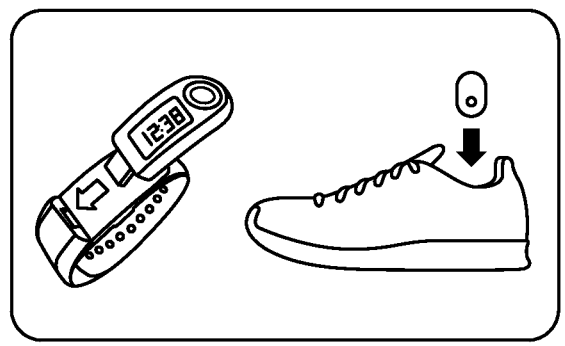
Figure 58:
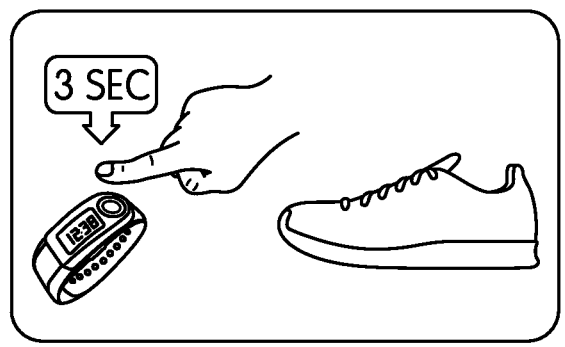
Figure 59:
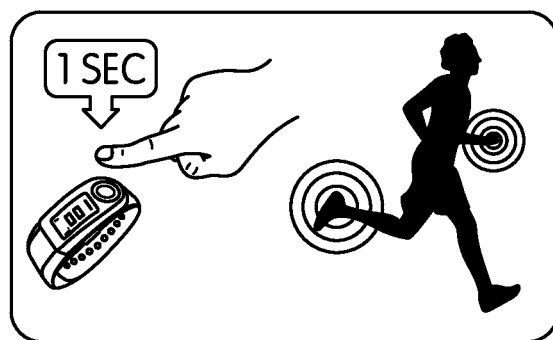
Figure 60:
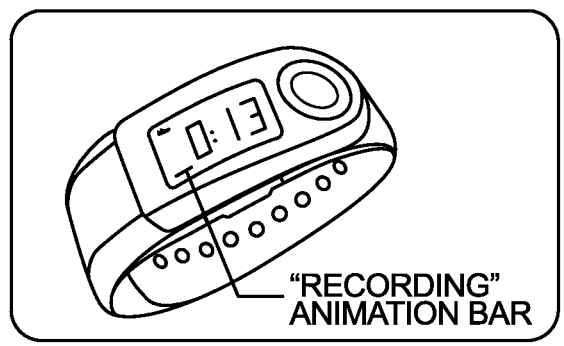
Figure 61:
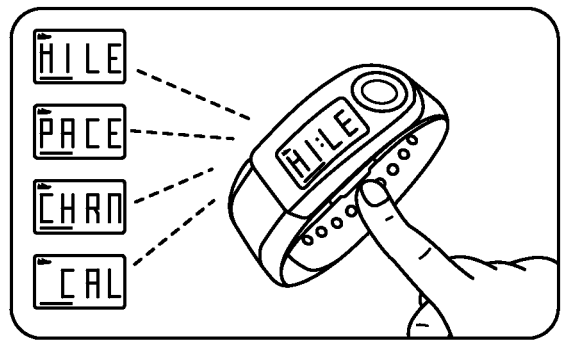
Figure 62:
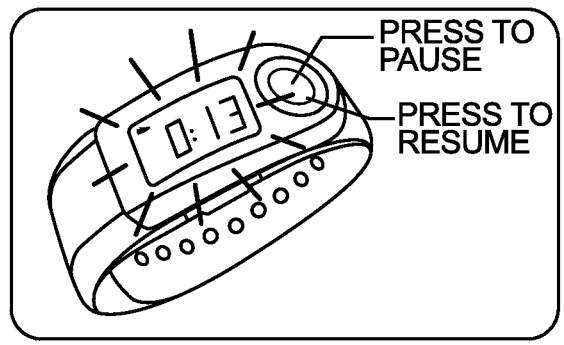
Figure 63:
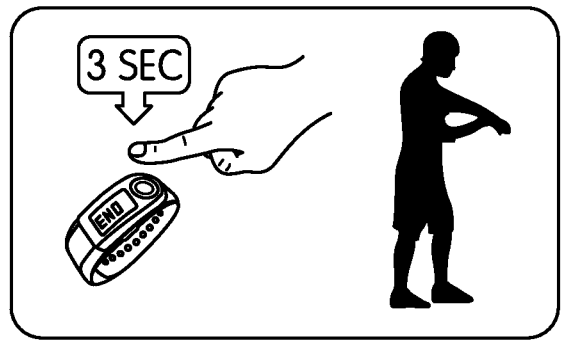
Figure 64:
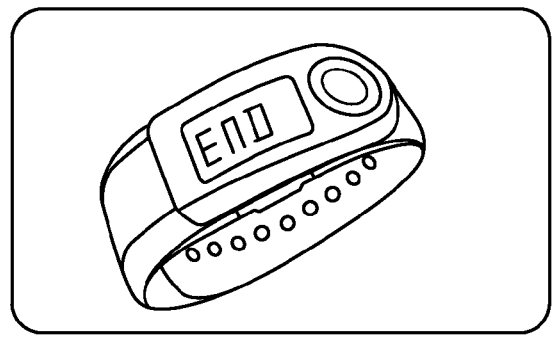
Figure 65:
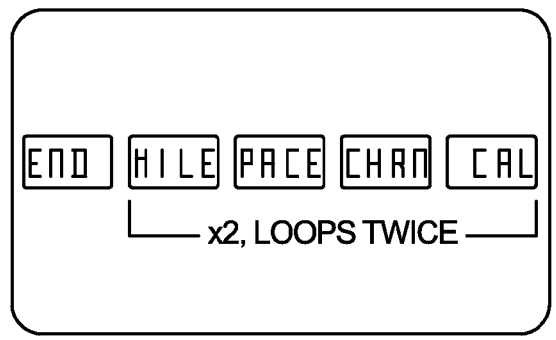
Figure 66:
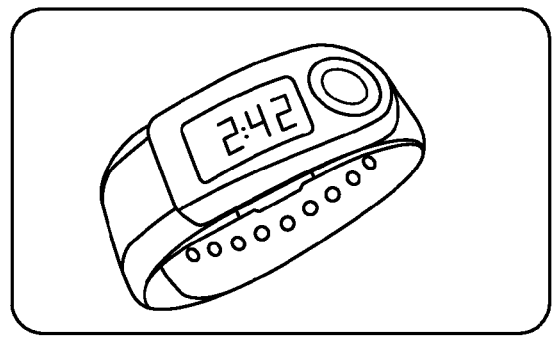
Figure 67:
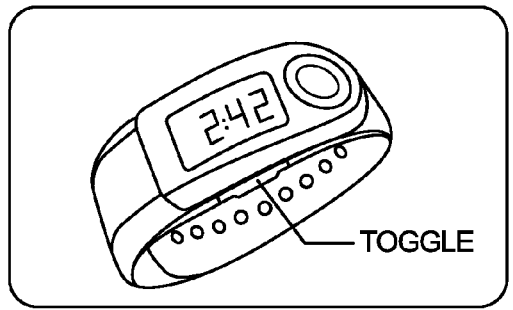
Figure 68:
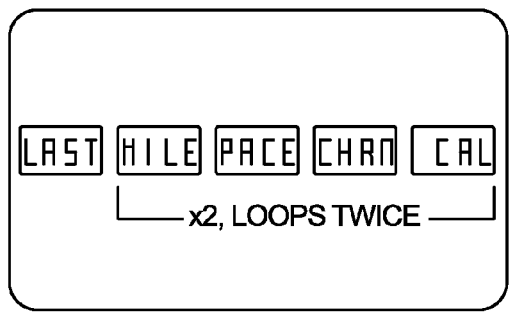
Figure 69:
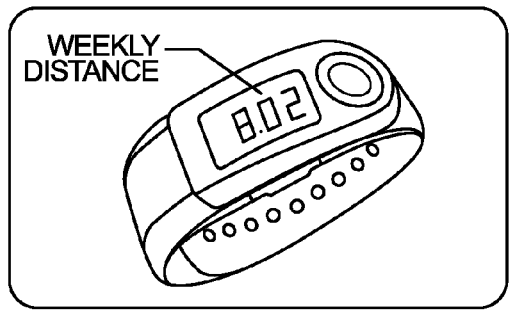
Figure 70:
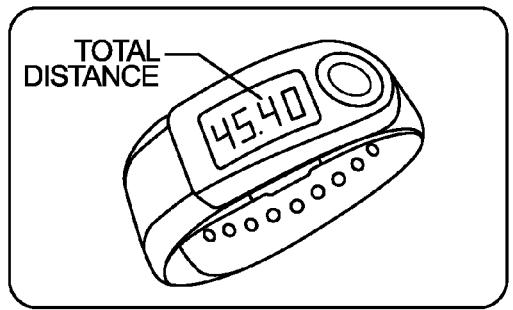
Figure 71:
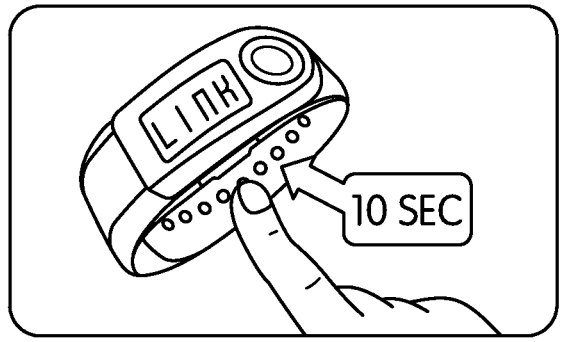
Figure 72:
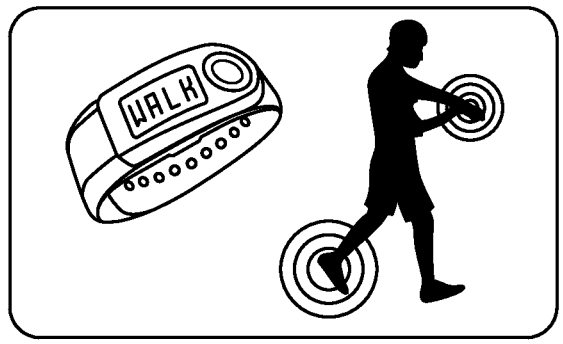
Figure 73:
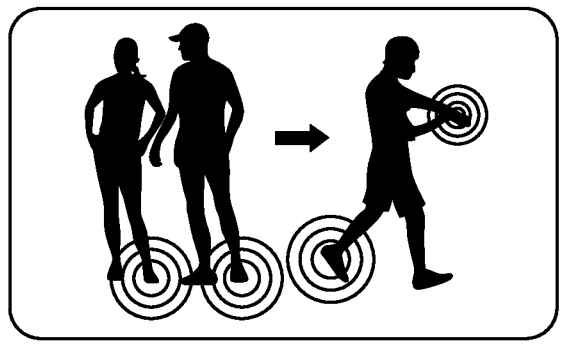
Figure 74:
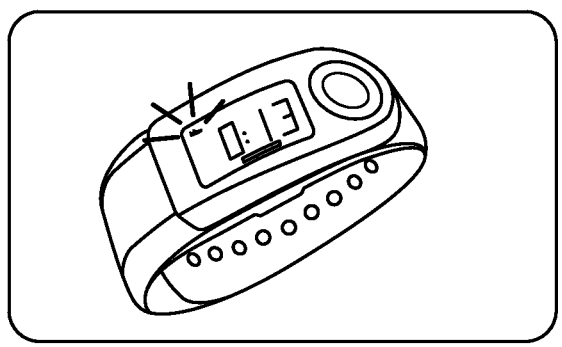
Figure 75:
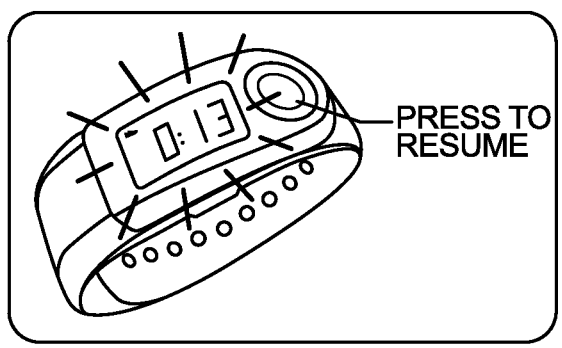

FIGS. 54-55 discloses Utility Menu windows. These windows, depending on the operating system, can be used as an alternate method for getting to settings, battery status and the like.

Figure 76:
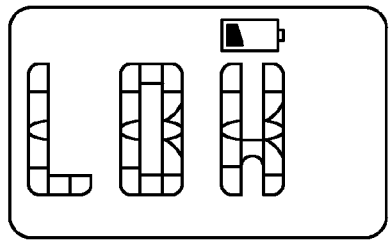
Figure 77:
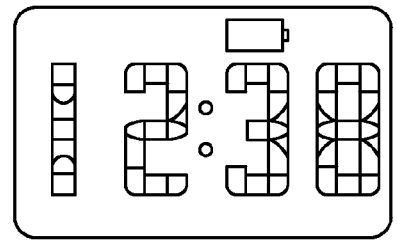
Figure 78:
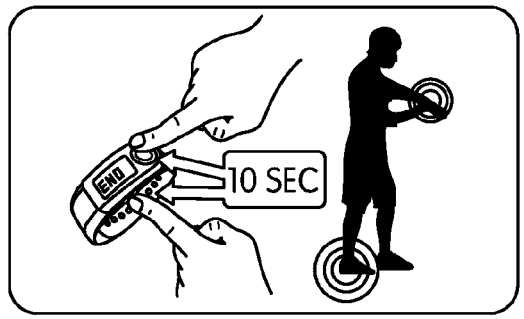
Figure 79:
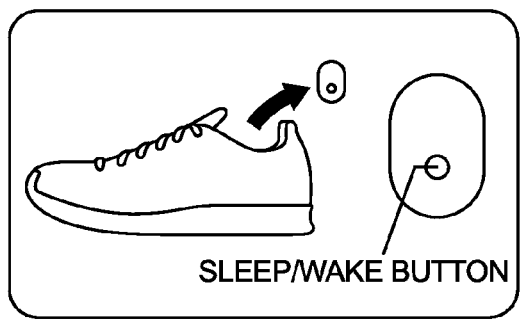
Figure 80:
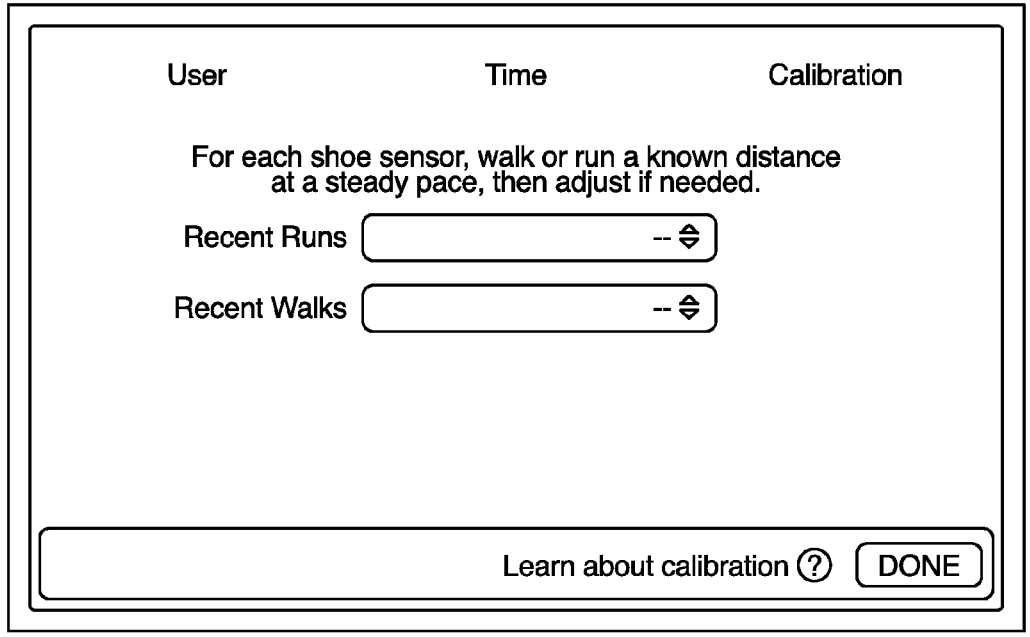

FIGS. 56-79 disclose additional operational features on the use of the wearable device assembly 14, such as use of the toggle buttons during a run as well as procedures when ending a run. For example, upon ending a run, the user can use the toggle buttons to review the data just recorded regarding the run. While the wearable device assembly 14 may be initially linked to a sensor, the assembly 14 is capable of being linked to multiple sensors. In one exemplary embodiment, the assembly 14 can link to 8 sensors. This is very helpful if the user performs athletic activity in more than one pair of shoes. FIGS. 76 and 77 provide additional information regarding the memory and battery associated with the wearable device assembly 14. FIGS. 45-49 disclose additional information regarding uploading of recorded run data to a website dedicated to tracking athletic performance.

The calibration module of the present invention can be configured to provide various additional features for enhancement of the device assembly 14.

In one exemplary embodiment, the calibration module is capable of storing multiple sets of calibration values for a user. Each calibration value is designed to be applicable to a specific pace range. The calibration module can then be configured to use appropriate calibration values depending on the pace of the walk or run of the user. Thus, as the user varies foot contact time, the appropriate set of calibration values is applied to calculate pace from the measured foot contact time. For example, the calibration information could include information for a slow pace, a medium pace and a fast pace. Based on the values read by the sensor 12, the calibration module will use the appropriate value to calibrate. Thus, if the run was done at a fast pace, the calibration module will calibrate using information corresponding to a fast pace.

As discussed above, the calibration module may be configured to store unique calibration values for each of a plurality of shoe sensors. This enables different calibrations for different shoes. For example, a user may wear different shoes for different training regimens or styles. The user interface associated with the calibration module can provide additional queries for a user to specify the type of training being performed and the calibration performed accordingly. The user can decide which runs/walks to calibrate based on which sensors were used for which runs/walks. It is understood that the software could be configured to provide a field to identify the sensor. It is further understood that even with multiple sensors, the assembly 14 will understand which particular sensor the assembly 14 is communicating with.

The calibration module may also be configured to provide certain automatic calibrations. For example, a user may participate in a performance such as a race having a known distance, e.g., a 5k or 10k race. The calibration module can be configured to automatically calibrate the sensor 12 at the end of the event. Thus, the actual recorded series of foot contact times can be correlated to the known distance of the overall event.

The calibration module may relate to a linear relationship between foot contact time and pace, wherein foot contact time may be considered a Y-axis value and pace may be considered an X-axis value. A run or walk can be represented by a line utilizing the line algorithm, $y=mx+b$, wherein m equals the slope and b equals the Y-intercept. The calibration module may be configured such that the calibration methodology alters both the slope and y-intercept values for each user for each walk or run calibration values. The calibration module may also be configured such that only the y-intercept value for each walk and run calibration value is altered.

The calibration module may also consider additional physiological traits of the user. For example, a user's shoe size, height, inseam, gender or other traits can affect optimum calibration settings. Thus, the user interface associated with the user interface may query the user to enter certain physiological traits during the calibration procedure. Additional calibration settings can then be utilized that are associated with the physiological traits. It is understood that a combination of such traits could be utilized in the calibration process. This feature can also be combined with other features described above to create an enhanced initial calibration (e.g., factory set, or "out-of-box" calibration) as well as an enhanced subsequent calibration.

As explained above, web-based map settings can be used to determine the known distance regarding a calibration walk or run. When global positioning system (GPS) data is available and determined to be accurate, the calibration module can be configured to automatically calibrate the sensor. In such fashion, the sensor 12 can be more accurate during times when GPS is not available such as during indoor activity or under heavy tree cover.

The calibration module can also be configured such that the module is operable with a sensor 12 that is linked with multiple athletic performance monitoring devices. For example, the user may use the device assembly 14 with a sensor 12 as well an additional monitoring device that is also linked with the sensor 12. The additional monitoring device could take various forms such as a traditional wristwatch having appropriate athletic functionality as described herein, a mobile phone, digital music player, or other type of mobile device. The calibration module can be configured such that the module is capable of distinguishing between different monitoring devices. Thus, if a user calibrates a run performed with a sensor 12 and the device assembly 14, and then the user performs a run using the sensor 12 with a different type of athletic performance monitoring device, the module will instruct the different monitoring device to record data based on the calibration done for the sensor 12 and the device assembly 14.

Conclusion

While the invention has been described with respect to specific examples including presently preferred modes of carrying out the invention, those skilled in the art will appreciate that there are numerous variations and permutations of the above described systems and methods. For example, various aspects of the invention may be used in different combinations and various different subcombinations of aspects of the invention may be used together in a single system or method without departing from the invention. Also, various elements, components, and/or steps described above may be changed, changed in order, omitted, and/or additional elements, components, and/or steps may be added without departing from this invention. Thus, the invention should be construed broadly as set forth in the appended claims.

The invention claimed is:

1. An athletic performance monitoring system for a user wherein the user utilizes a shoe-based sensor, the system comprising:
    a device having a USB connector, the device connected to a carrier configured to be worn by the user, the device having a controller configured to communicate with the sensor to record an athletic performance of the user, the athletic performance recording including measuring a distance traversed by the user;
    a calibration module operably associated with the device, the calibration module configured to display the measured distance traversed by the user wherein the user can compare the measured distance to a known distance associated with the athletic performance and adjust the measured distance to correspond to the known distance, wherein the known distance is determined by the calibration module based on an average of distances traversed during a plurality of prior athletic performances.

2. The system of claim 1 wherein the device measures a distance walked by the user as the measured distance.

3. The system of claim 1 wherein the device measures a distance run by the user as the measured distance.

4. The system of claim 3 wherein the user runs at a pace corresponding to a pace to be run during a race.

5. The system of claim 1 wherein the known distance is generally between 0.25 miles and 1.25 miles.

6. The system of claim 1 wherein the calibration module is located on a computer, the device being connected to the computer via the USB connector, wherein the measured distance traversed is transferred from the device to the computer and wherein the computer displays the measured distance traversed.

7. The system of claim 6 wherein calibration module is configured to receive user adjustments to the measured distance traversed via the computer.

8. The system of claim 1 wherein the calibration module is located on a remote website, the device being connected to a computer via the USB connector wherein the computer is in communication with the remote website, wherein the measured distance traversed is transferred from the device to the computer and to the website and wherein the website displayed the measured distance traversed on the computer.

9. The system of claim 8 wherein the calibration module is configured for the user to adjust the measured distance traversed via the computer.

10. The system of claim 8 wherein in response to plugging the device into the computer, the measured distance traversed is automatically uploaded to the calibration module.

11. The system of claim 1 wherein the known distance is further determined based on one or more distances determined by a web-based mapping service.

12. A calibration system for use with an athletic performance monitoring device for a user wherein the user utilizes a shoe-based sensor in communication with the device, the device having a controller configured to communicate with the sensor to record an athletic performance of the user, the athletic performance recording including measuring a distance traversed by the user, the system comprising:
    a calibration module configured to be operably associated with the device, the calibration module configured to display the measured distance traversed by the user wherein the user can compare the measured distance to a known distance associated with the athletic performance and adjust the measured distance to correspond to the known distance, wherein the calibration module is further configured to determine the known distance based on an average of distances traversed during a plurality of prior athletic performances.

13. The calibration system of claim 12, wherein the adjustment of the measured distance to correspond to the known distance is performed based on an adjustment formula and wherein the calibration module is further configured to modify the adjustment formula based on one or more additional athletic performances of the user.

* * * * *